United States Patent [19]

Feola et al.

[11] Patent Number: 5,439,882
[45] Date of Patent: Aug. 8, 1995

[54] BLOOD SUBSTITUTE

[75] Inventors: Mario Feola; Jan S. Simoni, both of Lubbock; Peter C. Canizaro, deceased, late of Lubbock, all of Tex., by Hana Illner, legal representative

[73] Assignee: Texas Tech University Health Sciences Center, Lubbock, Tex.

[21] Appl. No.: 61,763

[22] Filed: May 14, 1993

Related U.S. Application Data

[63] Continuation-in-part of Ser. No. 654,764, Feb. 12, 1991, abandoned, which is a continuation-in-part of Ser. No. 459,071, Dec. 29, 1989, abandoned.

[51] Int. Cl.$^6$ ............... A61K 38/42; A61K 35/14; C07K 14/805
[52] U.S. Cl. ................... 514/6; 514/832; 530/385; 530/829
[58] Field of Search ............ 514/6, 832; 530/385, 530/829

[56] References Cited

U.S. PATENT DOCUMENTS

| | | | |
|---|---|---|---|
| 3,864,478 | 2/1975 | Bonhard | 530/385 |
| 4,001,200 | 1/1977 | Bonsen | 530/385 |
| 4,001,401 | 1/1977 | Bonsen et al. | 514/6 |
| 4,061,736 | 12/1977 | Morris et al. | 514/6 |
| 4,100,149 | 7/1978 | Meiller | 530/362 |
| 4,336,248 | 6/1982 | Bonhard | 530/354 |
| 4,377,512 | 3/1983 | Ajisaka | 530/385 |
| 4,401,652 | 8/1983 | Simmonds et al. | 530/385 |
| 4,473,494 | 9/1984 | Tye | 530/385 |
| 4,473,496 | 9/1984 | Scannon | 530/385 |
| 4,473,498 | 9/1984 | Schlafer | 534/641 |
| 4,526,715 | 7/1985 | Kothe et al. | 530/385 |
| 4,584,130 | 4/1986 | Bucci et al. | 530/385 |
| 4,598,064 | 7/1986 | Walder | 514/6 |
| 4,600,531 | 7/1986 | Walder | 530/385 |
| 4,670,417 | 6/1987 | Iwasaki | 514/6 |
| 4,777,244 | 10/1988 | Bonhard | 530/385 |
| 4,780,210 | 10/1988 | Hsia | 210/638 |
| 4,826,811 | 5/1989 | Sehgal | 514/6 |
| 4,831,012 | 5/1989 | Estep | 514/6 |
| 4,857,636 | 8/1989 | Hsia | 530/385 |
| 4,861,867 | 8/1989 | Estep | 530/385 |

(List continued on next page.)

OTHER PUBLICATIONS

DeLoach et al. (1986) Anal. Biochem. 157:191-198.

Reed, et al., "High-Performance Liquid Chromatography Analysis of Nanomole Levels of Glutathione, Glutathione Disulfide, and Related Thiols and Disulfides," Analytical Biochemistry, 106:55-62 (1980).

Feola, et al., "Improved Oxygenation of Ischemic Myocardium by Hemodilution with Stroma-Free Hemoglobin Solution," Chest, 75:369-375 (1979).

Simoni, et al., "Biocompatibility of Hemoglobin Solutions. II. The Inflammatory Reaction of Human Monocytes and Mouse Peritoneal Macrophages," Artifical Organs, 14(2):98-109 (1990).

(List continued on next page.)

Primary Examiner—Michael G. Wityshyn
Assistant Examiner—Nancy J. Gromet
Attorney, Agent, or Firm—Cox & Smith Incorporated

[57] ABSTRACT

An improved blood substitute comprises purified hemoglobin, preferably bovine, cross-linked intramolecularly with periodate-oxidized ATP (o-ATP) and intermolecularly with periodate-oxidized adenosine (o-adenosine), combined with reduced glutathione (GSH), and optionally enriched with mannitol, non-electrolytes, and/or electrolytes. The blood substitute has prolonged intravascular persistence, can sustain plasma volume, has low oxygen affinity, can work as a physiological oxygen carrier, has vasodilator activity and can reduce the vasoconstriction that follows hemorrhage. A method of treating a human afflicted with acute blood loss and/or a sickling crisis of sickle cell anemia comprises intravenously administrating to the human an effective volume of the blood substitute.

52 Claims, 8 Drawing Sheets

EXAMINATION BY ISOELECTRONIC FOCUSING

A. Pharmacia Standard, pI 3 - pI 9
B. Hemolysate.
C. Hemoglobin after pasteurization (60 deg. C for 9 hrs, and 70 deg. C for 1 hr)
D. Hemoglobin after centrifugation with chloroform.
E. oATP Hb
F. oATP - oADENOSINE - GSH Hb SOD - Superoxide Dismutase
CA  - Carbonic Anhydrase IEF Shows both the purification of hemoglobin and the shift of Isoelectronic point from 6.8 to 6.1.

U.S. PATENT DOCUMENTS

| | | | |
|---|---|---|---|
| 4,876,241 | 10/1989 | Feldman et al. | 514/6 |
| 4,920,194 | 4/1990 | Feller | 530/385 |
| 4,978,619 | 12/1990 | Kajiwara | 435/182 |
| 5,028,588 | 7/1991 | Hoffman | 514/6 |
| 5,084,558 | 1/1992 | Rausch | 530/385 |
| 5,128,452 | 7/1992 | Hai et al. | 530/385 |
| 5,194,590 | 3/1993 | Sehgal et al. | 530/385 |

OTHER PUBLICATIONS

Feola, et al., "The Toxicity of Erythrocytic Stroma," The Red Cell: Seventh Ann Arbor Conference, pp. 361"382 (1989).

Feola, et al., "Nephrotoxicity of Hemoglobin Solutions," Biomaterials, Artificial Cells & Artificial Organs, vol. 18(2):233–249 (1990).

Simoni, et al., "Evaluation of anion-exchange liquid chromatography for purification of hemoglobin from peptides and other proteins," Analytica Chimica Acta, 249:169–183 (1991).

Feola, et al., "Clinical Trial of a Hemoglobin Based Blood Substitute in Patients With Sickle Cell Anemia," Dept. of Surgery, TTUHSC 1992.

Khym, et al., "Characterizations and Some Chemical Reactions of Periodate-oxidized Nucleosides," Journal of Aemrican Chemical Society, vol. 82:6380–6386 (1960).

Feola, et al., "Quality Control of Hemoglobin Solutions. I. The Purity of Hemoglobin Before Modification," Artif. Organs, vol. 15, No. 3, 1991.

Simoni, et al., "Generation of Free Oxygen Radicals and the Toxicity of Hemoglobin Solutions," Biomat., Art. Cells, Art. Org. 18(2):189–202 (1990).

Feola, et al., "Toxic Factors In The Red Blood Cell Membrane," The Journal of Trauma, vol. 29:1065–1075 (1989).

Feola, et al., "Toxicity of Polymerized Hemoglobin Solutions", Surgery, Gynecology & Obstetrics, 166:211–222 (1988).

Feola, et al., "Complement Activation and Toxicity of 'Stroma-Free Hemoglobin Solutions' in Primates", Circulatory Shock, vol. 25:275–290 (1980).

DeVenuto, et al., "Characteristic of stroma-free hemoglobin prepared by crystallization", General Laboratory and Clinicial Medicine, vol. 89:509–514 (1977).

Feola, et al., "Development of Bovine Stroma-Free Hemoglobin Solutions as Blood Substitute", Surgery, Gynecology & Obstetrics, vol. 157:399–408 (1983).

Scannon, "Molecular modifications of hemoglobin", Critical Care Medicine, vol. 10:261–265 (1982).

Greenberg, et al., "Modificiation of Hemoglobin-Ring Open Dials", Advances in Blood Substitute Research, Alan R. Liss, Inc., pp. 9–17 (1983).

Moss, et al., "Hemoglobin Solution—From Tetramer to Polymer", Biomaterials, Artificial Cells and Artificial Organs, vol. 16(1–3):57–69 (1988).

DeVenuto, et al., "Preparation and Evaluation of Pyridoxalated-Polymerized Human Hemoglobin", Journal of Surgical Research, vol. 34:205–212, 1983.

Feola, et al., "Biocapability of Hemoglobin Solutions. I. Reaction of Vascular Endothelial Cells to Pure and Impure Hemoglobins", Artificial Organs, vol. 13(3):209–215 (1989).

Estep, et al., "Virus Inactivation in Hemoglobin Solutions by Heat", Biomaterials, Artificial Cells & Artificial Organs, vol. 16(1–3):129–134 (1988).

Feinstrone, et al., "Inactivation of Hepatitis B Virus and Non-A, Non-B Heptatitis by Chloroform," Infection & Immunity, vol. 41:816–821 (1983).

Feola, et al., "Immunological biocompatibility of hemoglobin solutions", La Trasfusione del Sanque (Italian), vol. 33-121-128 (1988).

Chaudry, et al., "Overview of Hemorrhagic Shock", Pathophysiology of Shock Anoxishemi, Balitmore, Md., 203–219 (1982).

C. Su, "Extracellular Functions of Nucleotides in Heart and Blood Vessels," Annual Review of Physiology, vol. 47:665–676 (1985).

Berne, "Regulatory Function of Adenosine", Martin Nijhoff Publishers, Boston, Mass. 1983.

Larson, "Functions of Glutathione Biochemical, Physiological, Toxicological, and Clinical Aspects", Raven Press, New York, 1983.

Freeman, et al., "Free Radicals and Tissue Injury," Laboratory Investigation, vol. 47:412–426 (1982).

Fiske, et al., "The Colorimetric Determination of Phosphorous", Journal of Biological Chemistry, vol. 66:375–380 (1925).

Easterbrook-Smith, et al., "Pyruvate Carboxylase: Affinity Labelling of the Magesium Adenosine Triphosphate Binding Site", Eur. J. of Biochem., vol. 62:125–130 (1976).

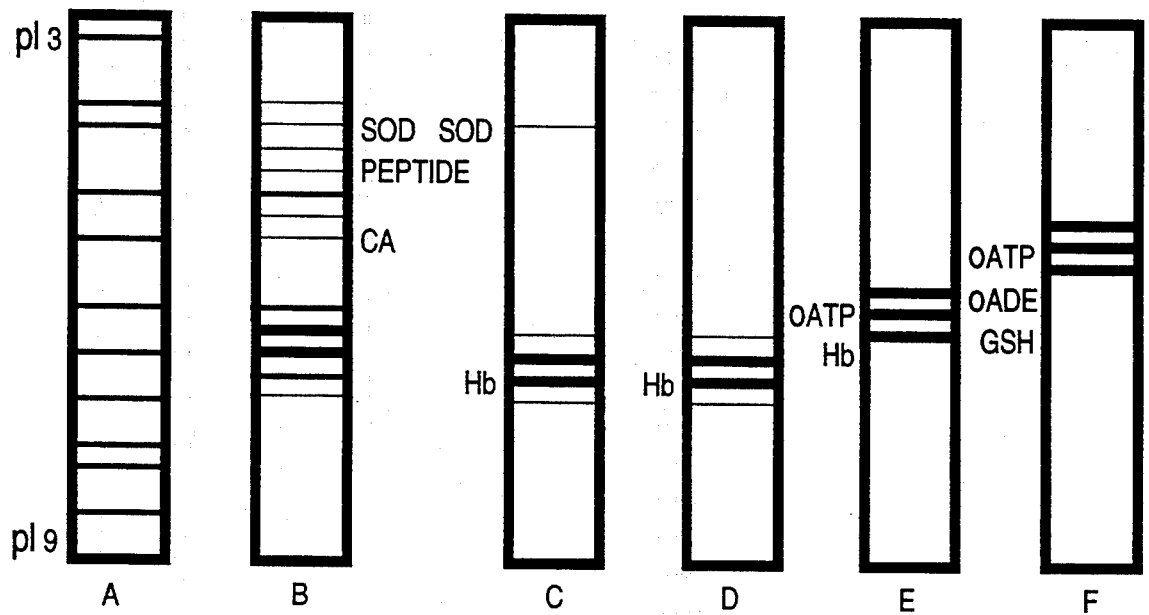

EXAMINATION BY ISOELECTRONIC FOCUSING

A. Pharmacia Standard, pl 3 - pl 9
B. Hemolysate.
C. Hemoglobin after pasteurization (60 deg. C for 9 hrs, and 70 deg. C for 1 hr)
D. Hemoglobin after centrifugation with chloroform.
E. oATP Hb
F. oATP - oADENOSINE - GSH Hb SOD - Superoxide Dismutase
CA  - Carbonic Anhydrase IEF Shows both the purification of hemoglobin and the shift of Isoelectronic point from 6.8 to 6.1.

Fig. 6

BLOOD SUBSTITUTE

This is a continuation-in-part application of application Ser. No. 07/654,764 filed on Feb. 12, 1991, now abandoned, which is a continuation-in-part of application Ser. No. 07/459,071 filed on Dec. 29, 1989, now abandoned. This application is also related to application Ser. No. 07/950,964 filed on Sep. 23, 1992, now abandoned, which is a continuation of application Ser. No. 07/459,071 filed on Dec. 29, 1989, now abandoned.

FIELD OF THE INVENTION

This invention relates to a blood substitute and to a method for its preparation. More particularly, it relates to a novel hemoglobin composition which is effective in sustaining life after severe hemorrhage in animals of various species, including humans, that is free of toxicity and blood transmissible diseases.

DESCRIPTION OF THE BACKGROUND

Blood performs many functions, all of which being vital. Severe hemorrhage or loss of blood endangers life for the following two main reasons: 1) the drop in circulating blood volume reduces tissue perfusion and produces ischemia; and 2) the reduction in oxygen transport impairs tissue oxygenation and produces hypoxia. The circulatory system reacts to these changes by producing vasoconstriction, which further aggravates ischemia and hypoxia. Ultimately, alterations of cell metabolism and function develop, which lead to shock and death.

In the context of this patent, a "blood substitute" is not a preparation that can replace blood in all of its functions, but an emergency resuscitative fluid that is capable of performing the following functions.

Restoring blood volume.
Transporting oxygen.
Reducing vasoconstriction.

This fluid, however, must be free of toxic side-effects, as well as of agents of disease such as bacteria and viruses.

For over 50 years, efforts directed to the development of a blood substitute have focused on hemoglobin (Hb), because this is the only substance capable of picking up enough oxygen from atmospheric air to serve as a physiological oxygen carrier. In addition, hemoglobin exerts the same colloid-osmotic pressure as serum albumin and can, therefore, serve as a plasma volume expander. However, up to the present time these efforts have not been successful due to a number of problems outlined below that have been slow to be recognized and difficult to be resolved.

(1) Toxicity brought about by contamination of hemoglobin with environmental bacterial endotoxins, stromal phospholipids, and non-heme proteins and peptides.
(2) High oxygen affinity of hemoglobin in solution interfering with release of oxygen to the tissues.
(3) Instability of Hb molecule and tendency to extravasation and rapid renal excretion.
(4) Tendency of Hb to autoxidation and generation of non-functional met-Hb and toxic oxygen free-radicals.
(5) Transmission by natural Hb of blood-related diseases, such as hepatitis and AIDS.

The problem of toxicity, i.e., the ability on the part of Hb solutions to activate the intravascular coagulation of blood and cause damage to the kidney was the first to be recognized. Rabiner in the 1960's popularized the notion that such toxicity was due to the stroma of red blood cells (fragments of red cell membranes) rather than to Hb. He emphasized the need of a stroma-free hemoglobin. However, this term has over the years belied the fact that a Hb truly free of all stromal elements has not been produced. The toxic factors of the red cell membrane were identified by the present inventor and collaborators as the aminophospholipids phosphatidylethanolamine (PE) and phosphatidyl serine (PS), which normally reside on its cytoplasmic side (M. Feola et al., "Toxic factors in the red blood cell membrane," *J. of Trauma*, 29:1065–1075, 1989). These compounds have a peculiar affinity for Hb and they are more difficult to remove from a Hb solution than other stromal components. When Hb contaminated with PE and PS is infused into experimental animals such as rabbits and monkeys in significant volumes, e.g., at least ⅓ of the animal's calculated blood volume, it causes a systemic inflammatory reaction characterized by activation of intravascular coagulation and complement, activation of leukocytes and platelets, and development of ischemic-inflammatory lesions in the vital organs (M. Feola et al., "Toxicity of polymerized hemoglobin solutions," *Surgery, Gynecology & Obstetrics*, 166:211–222 1988; M. Feola et al., "Compliment activation and the toxicity of stroma-free hemoglobin solutions in primates,"*Circulatory Shock*, 25:275–290, 1988).

A problem that has only recently been recognized is the easy contamination of Hb solutions with environmental bacterial endotoxins. Until the development of the limulus amoebocyte lysate test, the U.S. pharmacopoeia relied on the rabbit pyrogenicity test as the assay for tile detection of endotoxins. However, Hb contaminated with endotoxins at concentrations well below its pyrogenicity level was reported to cause the same kind of toxicity as Hb contaminated with aminophospholipids, since the toxic component of endotoxin is in fact a lipid (lipid A). Bacterial endotoxins can be removed from biological solutions by use of affinity chromatography columns, such as Detoxi-Gel columns (Pierce Chemical Co.). However, these columns cannot remove all the endotoxin present if the starting material contains more than 2 endotoxin units per milliliter, as determined by use of the "quantitative chromogenic limulus test" (QCL-1000, Whittaker M. D. Bioproducts) according to which 1 EU is equal to 0.1 nanograms of bacterial lipopolysaccharide.

Hb must be purified from non-heme proteins and peptides. While no toxicity has been associated with the presence of any particular protein, purification is mandated by the necessity of reducing the immunogenicity of natural Hb solutions. It has also been hypothesized that a peptide is responsible for the vasoconstrictor effect of Hb solutions observed in isolated organs such as the heart and kidney, and isolated arteries. A variety of methods for such purification are known to the art that include the following.

(1) Centrifugation and filtration, U.S. Pat. No. 3,991,181 to Coczi.
(2) Toluene extraction, U.S. Pat. Nos. 4,001,200 and 4,001,401 to Bonsen.
(3) Ultrafiltration, U.S. Pat. No. 4,526,715 to Kothe et al.
(4) Ultrafiltration plus acid precipitation, U.S. Pat. Nos. 4,136,093 and 4,336,248 to Bonhard et al.

(5) Ion-exchange chromatography, U.S. Pat. No. 4,100,149 to Meiller.
(6) Zinc precipitation, U.S. Pat. Nos. 4,473,494 and 4,529,719 to Tye.
(7) Crystallization, DeVenuto et al., Journal of Laboratory and Clinical Medicine 89: pp. 509–514 (1977).

None of the methods are totally satisfactory. The above methods (1)–(4) have intrinsic limitations as to the incapability for completely separating Hb from other proteins while methods (5)–(7) do not lend themselves to large-scale purification.

A problem recognized in the 1970's was the high oxygen affinity of Hb in solution. This is the property that regulates the ability of hemoglobin to pick up oxygen from air in the lungs and release it to the tissues. An expression of this property is the $P_{50}$ value or partial tension of oxygen at which Hb is 50% saturated. The lower the $P_{50}$, the greater the ability of hemoglobin to bind oxygen, and the more reduced its ability to unload oxygen into tissues. The $P_{50}$ of human blood is approximately 28 mm Hg whereas the $P_{50}$ of human Hb in solution is approximately 13 mm Hg. The difference is due to the fact that within the red blood cell Hb reacts with 2,3-diphosphoglycerate (2,3-DPG), which reduces the affinity of Hb for oxygen. Outside the red blood cell, that interaction is lost and thus Hb binds $O_2$ so tightly that it ceases to function as an $O_2$ carrier. To resolve this problem, Benesch et al. developed a covalent reaction of Hb with pyridoxal-5'-phosphate, a 2,3-DPG analogue. It was at first hoped that such reaction would both reduce oxygen affinity and stabilize the Hb molecule in tetrameric form. However, this failed to materialize. The present inventor and collaborators showed that bovine Hb in solution has the same $P_{50}$ value as human blood, and that its affinity for $O_2$ was regulated by chlorides rattler than by 2,3-DPG (M. Feola et al., "Development of a bovine stroma-free hemoglobin solution as a blood substitute," *Surgery, Gynecology & Obstetrics*, 157:399–408, 1983). Considering this favorable property, the large-scale availability of bovine RBCs and the low antigenicity of pure hemoglobin among mammals, there are advantages to the use of bovine hemoglobin as the basis for a blood substitute.

Another problem recognized in the 1970's was the rapid extravasation of hemoglobin with short intravascular persistence. This is generally attributed to a tendency of Hb tetramers, $\alpha_2\beta_2$, to dissociate into dimers, $2\alpha\beta$, which pass with greater ease through the blood capillaries. It now appears that the surface electric charge of tile protein also plays an important role, with electronegativity and low isoelectric point favoring intravascular persistence. Hemoglobin extravasation has the following several undesirable effects.

(1) The plasma volume-expanding effect is of short duration.
(2) Hb passage through the renal glomeruli generates an osmotic diuretic effect which reduces, rather than sustains, plasma volume.
(3) Hb reabsorption in the renal tubules causes injury to the tubular cells.
(4) Hb passage into the interstitial fluids causes edema and cell injury.

The prior art has focused exclusively on the prevention of Hb dimerization. For this purpose, the following three types of Hb modification have been developed so far.

(a) Intermolecular cross-linking or polymerization.
(b) Conjugation of Hb with other molecules.
(c) Intramolecular cross-linking of $\alpha$ or $\beta$ chains.

The most widely used of the above methods is the intermolecular cross-linking of Hb with glutaraldehyde disclosed in U.S. Pat. Nos. 4,001,200, 4,001,401, and 4,053,590 to Bonsen et al.; 4,061,736 to Morris et al.; 4,136,093 to Bonhard et al, the entire contents of which are incorporated herein by reference. Intermolecular cross-linking by itself suffers from the various drawbacks listed below.

(1) Glutaraldehyde is intrinsically toxic and the potential toxicity of its metabolic byproducts is unknown.
(2) Glutaraldehyde is very reactive and tends to form multiple bridges with various Hb sites, such as $\alpha$- and $\epsilon$-amino groups and sulphydryl groups. This leads to the formation of unpredictable numbers of molecular species.
(3) Polymerization is difficult to control and appears to continue during storage at 4° C., leading to formation of progressively larger polymers of increased viscosity and oxygen affinity.
(4) Non-specific nature of the cross-linking may still permit the presence of Hb dimers in solution.

As an alternative, Hb has been coupled with large-size molecules, such as dextran and hydroxyethylstarch (U.S. Pat. No. 4,064,118), polyethylene or polypropylene glycols (U.S. Pat. No. 4,412,986), inulin (U.S. Pat. No. 4,377,512), and poly-alkylene oxide (U.S. Pat. No. 4,670,417). However, these conjugated hemoglobins have increased oxygen affinity and tend to acquire unfavorable properties peculiar to the coupling substances. Intramolecular cross-linking has been achieved by the use of "diaspirin" esters (U.S. Pat. Nos. 4,529,719 to Tye; 4,598,004 to Walder); and "periodate-oxidized adenosine triphosphate" (o-ATP) (Scannon, F. J., "Molecular modification of hemoglobin", Critical Care Medicine 10:261–265(1982); Greenburg, A. G., and Maffuid, P. W., "Modification of hemoglobin—Ring opened diols", Advances in Blood Substitute Research, Liss, Alan R., New York, pp. 9–17 (1983)). However, the diaspirin-hemoglobins still have short intravascular persistence, with a half-life of 3–4 hours, and the ATP-hemoglobins have been found unsatisfactory due to high levels of met-Hb, high oxygen affinity and short half-life.

Significant progress has been reported by reacting human Hb with pyridoxal-5'-phosphate and glutaraldehyde to yield polymerized pyridoxalated Hb ("poly-PLP-hemoglobin"), i.e., a hemoglobin allegedly with both low oxygen affinity and prolonged intravascular persistence (Moss, G. S., et al., "Hemoglobin solution—From tetramet to polymer," Biomaterials, Artificial Cells and Artificial Organs 16(1–3):57–69(1988); DeVenuto, F. and Zegna, A., "Preparation and evaluation of pyridoxalated-polymerized human hemoglobin", J. Surgical Research 34:205–212(1983)). Pyridoxalation, however, was found to interfere with polymerization so that much of the pyridoxalated Hb would remain unpolymerized, while the polymerized Hb would be non-pyridoxalated. As consequence thereof, after infusion of the solution, the Hb with good $O_2$ transport function would be rapidly excreted via the kidney, while the Hb remaining in the circulation would be of high $O_2$ affinity.

Over the past few years, questions have been raised concerning an intrinsic toxicity of hemoglobin. On one hand, experimental observations have been reported of a vasoconstrictor effect of Hb. On the other, Hb tends to autoxidize to met-Hb, i.e., the heme iron oxidizes from the ferrous +2 to the ferric +3 state, generating toxic oxygen free-radicals. In view of this, it has been speculated that Hb may act as a pro-oxidant when infused into the circulation. This would produce the lipoperoxidation of cell membranes and cause injury to cell structures. Both these effects, vasoconstriction and generation of oxygen free-radicals would aggravate rather than alleviate the ischemic-hypoxic injuries caused by hemorrhage. Previous experimental studies by the present inventor and collaborators show that both vasoconstriction and the generation of radicals may be controlled by implementation of the following three steps.

(1) Complete purification of Hb.
(2) Preparation and stabilization of a Hb with low levels of met-Hb formation.
(3) Addition of oxygen radical-scavengers (M. Feola et al., "Biocompatability of hemoglobins solutions. I. Reactions of vacular endothelial cells to pure and impure hemoglobins," *Artificial Organs*, 13(3):209–215, 1989).

Finally, the administration of native Hb solutions carries the risk of transmitting blood product-transmissible diseases. While bacteria and parasites may be easily removed by filtration or ultrafiltration, viruses represent a more serious problem. Two methods of virus inactivation are known to the art. One is a physical method which consists of pasteurizing hemoglobin in its deoxy-form at 60° C. and pH 7.5 for 10 hours. This method has been found to inactivate model viruses such as sindbis, polio, and pseudorabies viruses as well as the human immunodeficiency virus (HIV) (T. N. Estep et al., "Virus inactivation in hemoglobin solutions by heat," *Biomaterials, Artificial Cells & Artificial Organs*, 16(1–3):129–134 1988). The other is a chemical method that consists of chloroform treatment (S. M. Feinston et al., "Inactivation of hepatitis B virus and non-A, non-B hepatitis by chloroform," *Infection & Immunity*, 41:816–821, 1983). Both methods, however, produce significant denaturation of Hb, unless special measures are taken.

Thus, there still exists a need for an improved blood substitute, which is stable, has low oxygen affinity, lacks toxicity and is free from blood-transmissible disease particles.

SUMMARY OF THE INVENTION

The present invention relates to a composition of matter and method of preparing same which is useful as a blood substitute and comprises purified mammalian hemoglobin (Hb), preferably bovine Hb, cross-linked intramolecularly with ATP (o-ATP), e.g., periodate-oxidized ATP, and intermolecularly with adenosine (o-adenosine), e.g., periodate-oxidized adenosine, reacted with reduced glutathione (GSH), and optionally dissolved in a non-electrolytic aqueous solution, and enriched immediately before use, with, e.g., mannitol, electrolytes, and optionally other pharmaceutically-acceptable additives.

This invention also relates to a method of preparing a composition suitable as a blood substitute, comprising separating Hb from bacterial endotoxins, stromal phospholipids; and or non-Hb proteins and peptides;

converting hemoglobin in solution to carboxy-hemoglobin;

reacting the carboxy-hemoglobin with o-ATP to effect predominantly intramolecular cross-linking of hemoglobin;

reacting the carboxy-hemoglobin with o-adenosine to effect predominantly intermolecular cross-linking of hemoglobin;

adding glutathione, e.g., reduced glutathione, to the solution to quench the o-adenosine cross-linking reaction and to lower the isoelectric point of Hb;

converting the cross-linked carboxy-hemoglobin to cross-linked oxy-hemoglobin; and optionally forming a pharmaceutically-acceptable cross-linked hemoglobin solution.

The resulting product is stable, has a circulatory half-life of about 24 hrs, has low oxygen affinity and a $P_{50}$ value similar to that of blood, and is free of toxicity and blood-transmissible diseases.

This invention also relates to a method of treating a human with sickle cell anemia afflicted with a sickling crisis comprising intravenously administering to the human a volume of the blood substitute of the invention effective to ameliorate the sickling symptoms.

This invention also relates to a method of treating a human in need of blood replacement comprising intravenously administering to the human a volume of the blood substitute of the invention effective to replenish blood volume and/or function.

A more complete appreciation of the invention and many of the attendant advantages thereof will be readily perceived as the same becomes better understood by reference to the following detailed description when considered in connection with the following drawings.

BRIEF DESCRIPTION OF THE DRAWINGS

In FIG. 3A, non-Hb proteins are visible, located at retention times 17 and 51 minutes. In FIG. 3B, non-Hb proteins are no longer visible.

FIG. 6 shows examination by isoelectric focusing (IEF—Pharmacia).

Figure 1:
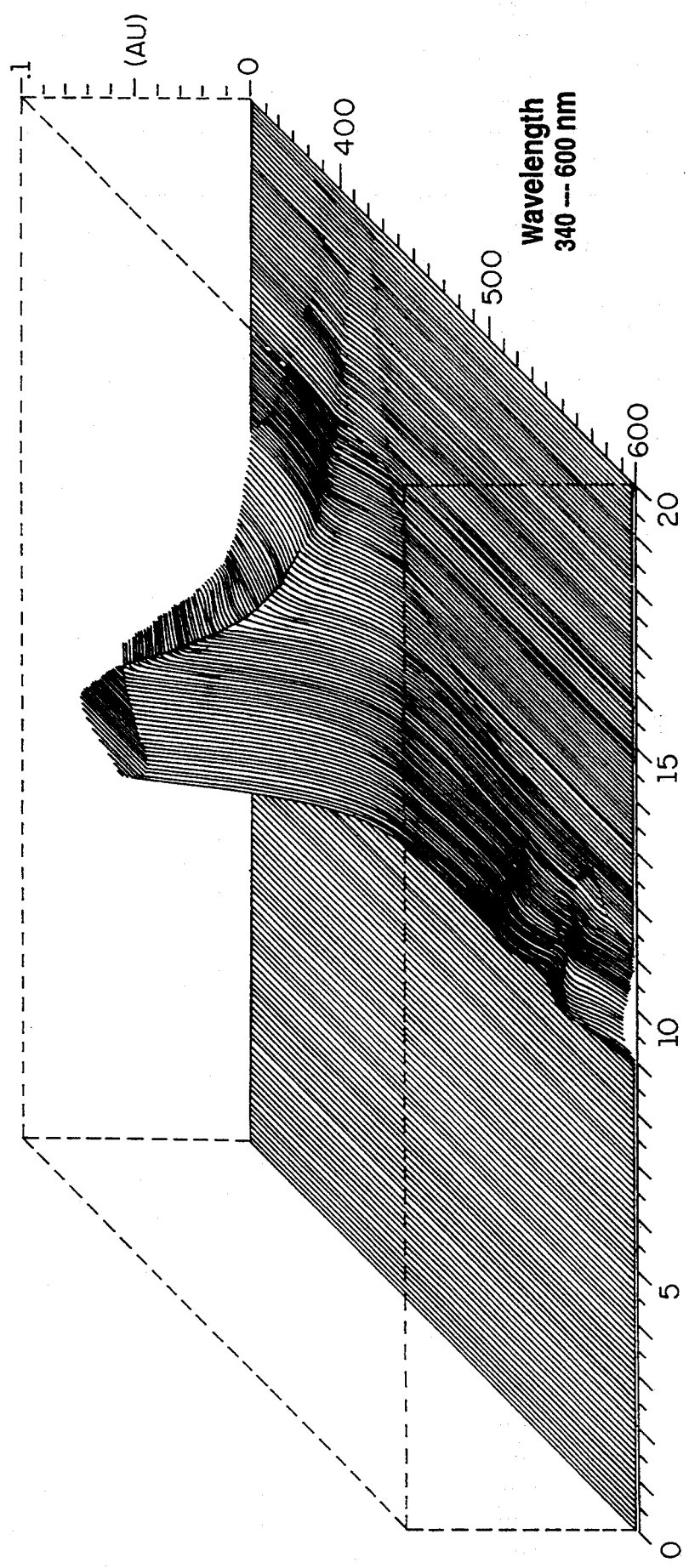
FIG. 1 shows a spectrum analysis of pure bovine Hb obtained by HPLC with a size-exclusion column. The chromatogram shows a single peak located at 9.4 minutes that identifies Hb in tetrameric form (64,000 daltons).

Other objects, advantages and features of the present invention will become apparent to those skilled in the art from the following discussion.

DESCRIPTION OF THE PREFERRED EMBODIMENTS

This invention arose from a desire by the inventors to improve on prior art treatments involving the replacement of human blood. The present technology provides a safe and effective means for blood replacement in cases of acute blood loss as well as for treating patients suffering from blood diseases which require a prompt and effective replacement of at least a portion of their blood volume in order to prevent and/or mitigate symptomatic crises. One example of such a situation is that of patients suffering from sickle cell anemia. When these patients go into a sickling crisis, they can be intravenously administered the blood substitute of this invention, which produces an unexpectedly superior mitigation of the symptoms brought about by the crisis.

The present invention provides a composition that comprises substantially pyrogen-free, microbe-free, active hemoglobin reacted with o-ATP and o-adenosine to form a cross-linked hemoglobin.

In one particularly preferred embodiment, the present composition utilizes bovine hemoglobin. However, other sources of hemoglobin may also be utilized herein.

In another preferred embodiment, the cross-linked hemoglobin of the invention is further reacted with reduced glutathione in order to stop the cross-linking reaction with o-adenosine, which also has the effect of lowering the isoelectric point of Hb. In still another preferred embodiment, the o-ATP comprises periodate-oxidized ATP and the o-adenosine comprises periodate-oxidized adenosine, arid the hemoglobin is intramolecularly cross-linked with the periodate-oxidized ATP and intermolecularly cross-linked with the periodate-oxidized adenosine to form a polyhemoglobin.

Since o-ATP and o-adenosine are two purine (P) derivatives, the product is denoted herein as Hb—P-P—GSH.

In another preferred embodiment of the invention the composition comprises hemoglobin, o-ATP, o-adenosine and glutathione in molar proportions of about 1:3:10:20. The cross-linked hemoglobin of the invention preferably has an about 130 to 390 kilodalton molecular weight, and more preferrably about 190 to 260 Kdalton molecular weight. A still more preferred form of the composition is that where the hemoglobin comprises less than about 5% met-hemoglobin.

In a most preferred embodiment the hemoglobin of the invention comprises bovine hemoglobin.

The hemoglobin (Hb) preparation of this invention combines the following favorable properties of its constituents.

(1) Effective oxygen-carrier. Bovine Hb, particularly, has a naturally low oxygen affinity ($P_{50}$ value of 28 mm Hg) that is not affected by the various chemical reactions.

(2) Effective plasma volume. Hb is cross-linked both intra- and inter-molecularly and thus has prolonged intravascular persistence (half life of 24 hours).

(3) vasodilating properties. Both purine derivatives combined with Hb relax norepinephrine-induced vasoconstriction.

(4) Does not exert a pro-oxidant effect due to the presence of reduced glutathione and mannitol.

The favorable properties of bovine Hb have been demonstrated (Feola, M., et al., "Development of a bovine stroma-free hemoglobin solution as a blood substitute", Surgery, Gynecology and Obstetrics 157:399–408(1983). Aside from its large-scale availability and the avoidance of transmissible diseases peculiar to human blood, AIDS in particular, bovine Hb dissolved in a saline solution has a $P_{50}$ value more than double that of human Hb (28 versus 13 mm Hg) and does not need 2,3-DPG modulation.

This invention also provides a blood substitute that comprises the substantially pyrogen-free, microbe-free, active hemoglobin (Hb) of the invention, cross-linked with o-ATP and o-adenosine, and a pharmaceutically-acceptable liquid carrier. In a most preferred embodiment the carrier is a pharmaceutically-acceptable solution, and more preferably an aqueous solution. Any such solution which will not interfere with the functional characteristics of Hb is suitable for use herein. The aqueous solution may further comprise non-electrolytes and/or electrolytes.

One embodiment of the invention provides a solution which is a non-electrolytic aqueous solution. This embodiment is shown in example 1. Examples of non-electrolytes that may be added to the aqueous solution of the cross-linked hemoglobin of the invention are human albumin, different plasma fractions, and plasma. However, any non-electrolyte that is pharmaceutically-acceptable and does not interfere with the oxygen-carrying function of the crosslinked hemoglobin of the invention may also be utilized, such as dextran and hydroxyethyl starch.

In another embodiment, the carrier is a pharmaceutically acceptable aqueous solution that contains electrolytes. This is shown in Examples 2–4. Typically, electrolytes that may be used in the blood substitute of the invention are sodium, potassium, calcium and magnesium cations, and chloride, bicarbonate, gluconate and sulfate anions. The following are solely examples, although others may also be utilized. injectable (sterile, pyrogen-free) water, pH about 8.1–8.2, adjusted by the addition of sterile pyrogen-free buffer, THAM solution, (Tromethamine Injectable; Abbott Laboratories, North Chicago, Ill.); injectable water-THAM solution plus added electrolytes such as 113 meq/l sodium chloride, 27 meq/l sodium bicarbonate, 4 meq/l potassium chloride, 5 meq/l calcium gluconate, 3.5 meq/l magnesium sulfate; electrolyte-balanced saline solution (Normosol R, pH 7.4, containing 140 meq/l sodium, 5 meq/l potassium, 3 meq/l magnesium, 98 meq/l chloride, 27 meq/l acetate, and 23 meg/l gluconate; Abbott Laboratories); and lactated Ringer's solution containing 130 meg/l sodium, 4 meq/l potassium, 3 meg/l calcium, 109 meq/l chloride, and 28 meg/l lactate (Abbott Laboratories) among others.

In accordance with one embodiment of the present invention, the oxygen affinity of bovine Hb can be further lowered by increasing the concentration of chloride ions in the blood substitute. This may be attained by adding about 10 to 25 meq/l chloride/l of blood substitute, and more preferably about 15 meq chloride/l of blood substitute.

With regard to potential immunological problems, the feasibility of Hb transfusions across different mammalian species has been well-demonstrated in the art. Pure bovine hemoglobin has been administered repeatedly, for up to 6 times, to rabbits and monkeys in volumes corresponding to ⅓ to ½ of calculated blood volumes without clinical evidence of reaction and without formation of antibodies detectable by Ouchterlony's test (Feola, M., et al., "Immunologic biocompatibility of hemoglobin solutions", Trasrusione del sangue (Italian) 33:121–128(1988)).

In order to produce a Hb solution free of bacterial endotoxins, the strategy used in the present method of preparation is, in general, one of preventing rather than correcting contamination. Given the affinity of endotoxin for hemoglobin, once significant contamination has occurred, purification is extremely difficult, if not impossible, to attain. The substantial prevention of contamination requires the following.

(1) The starting material to be minimally contaminated.
(2) The preparative steps to be carried out in a closed system.
(3) All surfaces coming in contact with Hb to be sterile and pyrogen-free.
(4) All chemicals to be pure.
(5) All solutions to be sterile and pyrogen-free.
(6) Quality control to be instituted at every step.

The most sensitive method for the detection of endotoxin is the "quantitative chromogenic limulus test" (QCL-1000, Whittaker Bioproducts). If the starting material, or the hemoglobin at any preparative step, is found to contain more than 2 EU/ml, it is discarded. By maintaining a low level of contamination throughout the process, complete purification can be achieved by final passage of the solution through an affinity chromatography column, such as the Detoxi-Gel (Pierce Chemical Company).

The same principle of avoidance of gross contamination coupled with final purification is applied to the removal of stromal phospholipids, and aminophospholipids in particular. To obviate stromal contamination, the present method incorporates known technology for red blood cell (RBC) dialysis and ultrafiltration (DeLoach, J. R., et al., Analytical Biochemistry 157:191–198(1986)). According to DeLoach's method, the RBCs are first dialyzed using a Travenol artificial kidney against a hypotonic phosphate solution until the RBC suspension reaches an osmolarity of about 150 to 200 mOsm/l, and more preferably about 160 mOsm/l. At this point, the RBCs assume a spherical shape and the pores of the cell membrane are stretched. The cells are then subjected to ultrafiltration through an about 0.1 μm pore Amicon filter under a column pressure of about 5 to 15 psi, and more preferably about 10 psi. Thus, Hb is "squeezed out" of the cells without disruption of the cell membranes. In accordance with the present invention, a single closed-system is utilized for both the dialysis and the ultrafiltration of the RBCs. This step is sterile, pyrogen-free and disposable. The dialysis fluid comprises, e.g., sterile, pyrogen-free deionized water adjusted to a pH of about 8.0 to 8.4, and more preferably about 8.2 with, e.g., a Tham solution, instead of a phosphate solution, which reduces hemoglobin oxidation. However, other non-electrolytes may also be utilized. The result of this process is a Hb solution comprising 3 to 5 mg/dl phospholipid as measured by the "Phospholipid Test Set" (Boeringer-Manheim Diagnostics, Indianapolis, Ind.), with only traces of the aminophospholipids PE and PS as determined by thin-layer chromatography. The residual phospholipid may be removed, e.g., by chloroform extraction. Because of the low level of phospholipid present, this step may be carried out with low concentrations of chloroform for short-time centrifugations. The denaturation of Hb may thus be prevented. The removal of phospholipid may, however, be undertaken by other means known in the art as long as care is exercised to avoid or minimize protein denaturation.

The same principles apply to the purification of Hb from non-heme proteins and peptides. In this case, a first step comprises the removal of all plasma proteins during the "purification" of red blood cells. The extraction of Hb from RBCs may be conducted herein without large-scale disruption of red cell membranes, thus also preventing contamination with stromal proteins. Hb purification may then be achieved by selective thermal precipitation (Belter, P. A., Cussler, E. L., Hu, W. S., Eds., Bioseparations, John Wiley Sons, New York, pp. 227–229 (1988)). In this method, the denaturation and the precipitation of proteins is attained by raising the temperature to about 56° to 72° C., and more preferably about 60° to 70° C. This treatment of the proteins follows first-order chemical kinetics with an Arrhenius temperature dependence. Thus, $$\frac{d|P|}{dt} = -\kappa |P|$$

wherein P is the dissolved protein concentration. The rate constant $\kappa$ is given by tile formula $$\kappa = \kappa_0 \, e^{E/RT}$$

wherein $\kappa_0$ is a characteristic constant, E/R is the activation energy of denaturation and T is the temperature. The energy of denaturation varies from one protein to another. Because E appears exponentially in the equation, it has a large effect when the temperature is even slightly changed. This energy is also affected by changes in pH. When saturated with carbon monoxide, the Hb (HbC0) is resistant to temperature-induced precipitation at a pH of about 7.6 to 7.8. Thus, the pasteurization of a HbCO solution may be conducted at a temperature of about 56° to 64° C. and more preferably at 60° C. for 9 hours, followed by pasteurization at a temperature of about 68° to 74° C., and more preferably about 70° C. for about 0.45 to 1.15 hours, and more preferably about 1 hour, at a pH of about 7.6 to 7.8, at a concentration of about 8 to 12 g/dl HbCO, and more preferably about 10 g/dl. These conditions precipitate all non-heme proteins with little denaturation of Hb. The absence of non-hemoglobin proteins in the solution as prepared by the present method has been verified by isoelectric focusing (IEF) and by size-exclusion and anionic-exchange high pressure liquid chromatography (HPLC). The non-denaturation of recovered hemoglobin was demonstrated by the absence of "smudging" of focused hands on IEF and by the preservation of its oxygen transport function (oxygen dissociation curves, $P_{50}$, Bohr effect).

A byproduct of the present purification is the inactivation of viruses. In fact, chloroform extraction has been found to inactivate a number of lipid-enveloped viruses, such as hepatitis B, non-A non-B hepatitis, vaccinia and pox viruses, both in plasma and serum (Feinston, S.M., et al., "Inactivation of Hepatitis B virus, and non-A, non-B hepatitis by chloroform", Infection and Immunity 41:816-821(1983)). Some viruses lacking lipids such as reoviruses may also be partially inactivated with chloroform. On the other hand, pasteurization at a temperature of about 56° to 64° C., and more preferably about 60° C. for about 9 to 12 hours, and more preferably about 10 hours, inactivates a number of non-lipid enveloped viruses as well as the human immunodeficiency virus (HIV) (Estep, T. N., et al., "Virus Inactivation in Hemoglobin Solutions by Heat", Biomaterials, Artificial Cells, and Artificial Organs 16(1-3):1-29-1343(1988)).

Because of the known undesirable effects of glutaraldehyde polymerization, the present method stabilizes the Hb molecule in tetrameric form by using a dialdehyde derivative of adenosine 5'-triphosphate (o-ATP). The ATP molecule has three basic components: the purine base adenine, the sugar D-ribose and a triphosphate chain as can be seen as shown below.

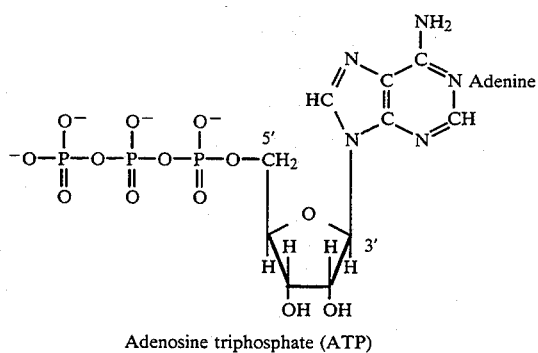

Adenosine triphosphate (ATP)

The oxidation of ATP with sodium periodate opens the ribose ring at the 2',3'-cis site and transforms the 2',3'-diol into the corresponding dialdehyde (Lowe, P. N., et al., "Preparation and chemical properties of periodate-oxidized adenosine triphosphate and some related compounds", Biochem. Soc. Transact. 7:1131-1133(1979)) as shown below.

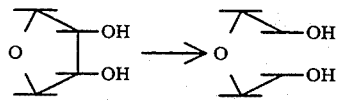

Each aldehyde group of the o-ATP molecule can react with the ε-amino group of lysine to form a Schiff base adduct of the following chemical formula.

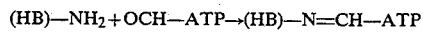

The 2,3-DPG pocket of Hb is the region within the Hb molecule that binds 2,3-DPG. Since this region contains two lysines, it is possible to use o-ATP to cross-link these groups to stabilize the molecule in its tetrameric form. The presence of the triphosphate chain increases the specificity of this reaction. This specificity has been demonstrated for other polyphosphates such as pyridoxal-5'-phosphate. The advantage of ATP over other compounds is provided by the adenine moiety. In vivo, ATP hydrolyzes to ADP, AMP and finally to adenosine. This hydrolysis has been found to produce beneficial pharmacologic effects such as vasodilation both in the systemic and pulmonary circulations. Additional beneficial effects have been demonstrated when ATP is given in combination with magnesium chloride ($MgCl_2$) in hemorrhagic shock. These beneficial effects include an improvement of the microcirculation, an improvement of cell membrane function and a "priming" effect on the restoration of intracellular adenine nucleotides (Chaudry, I. H., and Baue, A. E., "Overview of hemorrhagic shock", Pathophysiology of Shock, Anoxia and Ischemia, Cowley, R. A., and Trump, B. F., editors, Williams and Wilkins, Baltimore, Md., pp. 203-219 (1982)).

As noted above, previous attempts at cross-linking Hb with o-ATP were unsuccessful because the chemical reaction produced unacceptable levels of met-Hb (up to 30%), and the o-ATP-modified Hb still had a short intravascular persistence. In addition, ATP has an undesirable tendency to chelate divalent cations from the vascular system.

However, the oxidant effect of o-ATP is due to traces of iodate ($IO_4^-$ and $IO_3^-$) present in the compound. In fact, a complete purification of o-ATP (see, Example 10) substantially corrects that problem. In addition, the formation of met-Hb can be minimized by reaction of o-ATP with carboxy-Hb rather than with deoxy-Hb, as had previously been done. The reaction of o-ATP with HbCO takes place if the pH of the solution is reduced to about 7.25 to 7.15, and more particularly when reduced to about 7.20. With regard to the cation-chelating effect, we confirmed the report by Chaudry and Bauer (see above) that the addition of magnesium chloride ($MgCl_2$) in amounts equimolar with ATP eliminated this problem.

There is left, however, the problem of short intravascular persistence. The present inventors have found that intramolecularly cross-linked tetrameric Hb is still filtered through the renal glomeruli and causes damage to the renal tubules. Therefore, it is necessary to cross-link hemoglobin inter- as well as intra-molecularly, if adequate intravascular retention times are to be attained and renal damage to be avoided.

The present invention utilizes a second purine derivative, a dialdehyde derivative of adenosine or periodate-oxidized adenosine <o-adenosine) as a second cross-linking agent. The Hb molecule carries 44 lysine amino-groups on its surface. Thus, it is possible to use o-adenosine to bridge two or more of these groups to bind two or more of the Hb tetramers. The advantages of adenosine over other compounds are several. Due to the presence of adenine, adenosine has a vasodilator effect similar to that of ATP (Su, C., "Extracellular functions of nucleotides in heart and blood vessels", Annual Review of Physiology 47:665-676(1985)). In addition, adenosine inhibits platelet aggregation and improves glomerular filtration in the kidney. Both of these effects are beneficial after hemorrhage and reperfusion (Berne, R. M., Regulatory Functions of Adenosine, Martin Nijhoff Publisher, Boston, Mass. (1983)).

The reaction of Hb with o-adenosine was unknown prior to this invention. It is important that the reaction be carried out with hemoglobin in its carboxy (HbCO) form in order to reduce met-Hb formation. Finally, the reaction proceeds more slowly at lower temperatures, e.g., about 25° to 10° C., and very slowly at about 4° C. These conditions are desireable because they permit that the reaction be stopped at any time after the formation of the desired molecular aggregate. This permits the preparation of Hb polymers of different molecular sizes in a planned and reproducible fashion, which cannot be attained with other cross-linking agents such as glutaraldehyde. The cross-linking of Hb with o-adenosine may be stopped by adding reduced glutathione (GSH), which, like lysine, carries an ε-amino group. By entering this reaction, GSH becomes part of the Hb composition.

GSH is a preferred stopping agent since it is abundant within the red blood cell where its primary function is to work as an "oxidant trap" that protects hemoglobin from oxidant stress (Larson, A., Functions of Glutathione: Biochemical, Physiological, Toxicological and Clinical Aspects, Raven Press, New York (1983)). GSH protects hemoglobin in solution as well as within the erythrocytic environment. The cross-linking of Hb with o-adenosine followed by reaction with GSH produces an increase of electronegative charges on the surface of the Hb molecule with a reduction of the Hb's isoelectric point from about 6.8 to 6.1-6.2. This contributes to the stabilization of hemoglobin and prolongs its intravascular persistence by preventing its filtration through the kidney.

o-ATP and o-adenosine may be obtained from commercial sources (Sigma Chemical Co., St. Louis, Mo.) or prepared according to the methods described below as Examples 10 and 11. Reduced glutathione may be obtained from a commercial source.

Following these reactions and the reconversion of carboxy-hemoglobin to oxy-hemoglobin, the obtained compound (Hb—PP—GSH) may be dissolved into various media, depending on storage needs. If the solution is to be stored for several months, or even years, the (Hb—PP—GSH) may be left dissolved in "injectable", sterile, pyrogen-free water, pH about 8.1-8.2 adjusted by addition of 20 mM THAM solution. The present inventors have found that Hb dissolved in water, at an alkaline pH, pH 8.1-8.2, undergoes less autoxidation and can be stored for longer periods of time than Hb dissolved in an electrolyte solution, at about pH 7.4. In this case, electrolytes may be added to the solution immediately before use (see, examples above). If, on the other hand, the solution is to be used within hours or days, the (Hb—PP—GSH) may be directly dissolved in an electrolyte-balanced saline solution, such as Normal R (see, examples above). The compound may, alternatively, be dissolved into a lactated Ringer's solution(see, examples above) or a hypotonic or isotonic sodium chloride solution, among others. When the blood substitute of the invention is to be used for the treatment of hemorrhagic shock, magnesium chloride ($MgCl_2$) may be added to the solution, preferably immediately before use, in an amount about equimolar with the content of ATP in the composition. This has been found to complement the beneficial effects of ATP on the microcirculation, and to provide excess chloride ions which modulate downward the affinity of Hb for oxygen and provide better tissue oxygenation. It has also been found to control the divalent cation-chelating effect of ATP. Mannitol may be added preferably immediately before use since it is known to work as a scavenger of OH radicals, (the most toxic oxygen-derived free radicals, and perhaps of other radicals as well (Freeman, B. A., and Crapo, J. D., "Free radicals and tissue injury," Laboratory Investigation 47: 412-426 (1982)). Typically, mannitol may be added in an amount of about 0.5 to 2.0 mg/ml, preferably about 0.8 mg/ml of solution.

The present invention thus provides a composition useful as a blood substitute that is capable of (a) restoring and sustaining plasma volume.

(b) supplying the vital organs with oxygen. and (c) relieving vasoconstriction after hemorrhage.

It is also the object of the present invention to provide a method for the preparation of a blood substitute from hemoglobin.

The composition of the invention provides a blood substitute which is free of toxicity when administered to mammals, including humans, and devoid of blood-transmissible disease particles.

Other objects, features and advantages of the invention will become evident in light of the following detailed description of preferred exemplary embodiments according to the present invention.

EXAMPLES

A preferred process for preparing the complex product according to this invention comprises the following five steps.

(A) Purification of red blood cells,
(B) Extraction of hemoglobin,
(C) Purification of hemoglobin.
(D) Modification of hemoglobin by reaction with o-ATP, o-adenosine and glutathione.
(E) Preparation of final product $(Hb—PP—GSH)_n$.

EXAMPLE 1

Purification of Red Blood Cells (RBCs)

A preferred starting material of the composition of the invention is bovine blood as discussed above. However, the method of the invention for the preparation of the composition may be applied to other types of mammalian blood, including human blood, as the starting material. Bovine blood may be obtained from multiple healthy donors or from individual animals cleared for the slaughterhouse. In the first case, an adult cow is restrained, the neck is shaved and the skin prepared with antiseptic soap. Blood is drawn by puncture of the external jugular vein under aseptic conditions. Approximately 1,500 ml of blood can be obtained from one animal, collected into a 2-liter evacuated, sterile, pyrogen-free bottle containing 200 ml of ACD anti-coagulant (Virbac, Inc., Lenexa, Kans.). In the second case, after the animal is stunned prior to slaughtering, one side of the neck is quickly "prepared" and a trocar is inserted percutaneously into the carotid artery. Approximately 10 liters of blood can be removed from each adult cow. Blood from different animals is not mixed. The bottles are kept on ice in transit to the laboratory.

It is important, particularly when starting from bovine blood, that the RBCs (erythrocytes) be completely separated from white blood cells (leukocytes), platelets and plasma. This step reduces the load of non-heme proteins and other substances from which hemoglobin needs to be ultimately purified. Also, the removal of all leukocytes also removes any viruses associated with these cells such as cytomegalovirus, human immunodeficiency virus and others.

The RBCs are purified by a "spin-cool-filter" method. The "spin" step consists of multiple centrifugations carried out in closed-system fashion by use of a blood bank cell separator, such as the DIDECO system (Electromedics Inc., Englewood, Col.), in the following manner.

Centrifugation at 1,100 rpm at 15° C. for 20 minutes to remove platelets and plasma.

Centrifugation at 4,500 rpm at 15° C. for 10 minutes for more complete removal of plasma.

Washing (x 4) with isotonic saline solution (RBCs/saline 1:4) by centrifugation at 4,100 rpm at 4° C. for 10 minutes.

Final washing with isotonic Tham solution, pH 8.1–8.2 (Tham USP, Abbott Laboratories, North Chicago, Ill.). This allows the suspension of washed RBCs into an electrolyte-free, high-pH solution, which protects the hemoglobin from oxidation.

For the "cool" part of the process, the RBCs are stored within "transfer packs" (sterile, pyrogen-free plastic containers made by Fenwal Laboratories, Deerfield, Ill.) at 4° C. overnight, or for 18 hours. At low temperature, the white blood cells tend to aggregate into small clumps. For the "filter" step, the cells are passed through a 20μ cellulose filter, such as the "high capacity transfusion filter" made by Fenwal, which removes the leukocyte aggregates.

To ascertain the absence of leukocytes and platelets, cell counts are carried out by use of a Coulter cell counter, and the absence of proteins in the suspension is verified by routine chemical methods. The presence of bacterial endotoxins is determined by use of the "quantitative chromogenic limulus test" (QCL-1000, Whittaker Bioproducts, Walkersville, Md.).

EXAMPLE 2

Extraction of Hemoglobin

The extraction of hemoglobin from RBCs is carried out in two steps. First, one liter of RBCs suspended into isotonic Tham solution, pH 8.1–8.2, at the concentration of 20% (hematocrit 0.20) is dialyzed against 10 liters of hypotonic (230 mOsm/L) Tham solution by means of an artificial kidney with 0.20μ porosity, such as the "Krosflo II Filtration Module with 10 Ft$^2$ Surface Area" (Microgon Inc., Laguna Hills, Calif.). The dialysis is carried out until the dialysate becomes reddish in color (hemoglobin tinged). At this point, the RBCs are swollen to a spherical shape, and the stretched cell membranes become permeable to Hb. As second step, a 10 psi pressure is applied to the artificial kidney, squeezing the Hb out of the cells without disruption of cell membranes. The membrane "ghosts" are discarded after pass. As hemoglobin enters the hypotonic solution reservoir, volume is maintained in the RBC reservoir by the addition of Tham solution, 230 mOsm/L. The extracted hemoglobin is filtered through a 0.20μ filter, such as the "Posidyne I.V. Filter" (PALL Biomedical Inc., Fajardo, Puerto Rico), to remove residual particulate debris or microbial contaminants, and stored in "transfer packs" at 4° C.

The result of this process is a Hb solution that contains 3–5 mg/dl of phospholipids (measured by use of the "phospholipid test set," Boeringer-Manheim Diagnostics, Indianapolis, Ind.), with only traces of aminophospholipids PE and PS (determined by thin-layer chromatography).

Purification of Hemoglobin

This purification was carried out in the following four steps.

Example 3

Pasteurization of Hemoglobin in Carboxy Form (HbCO)

This step is carried out within a pre-sterilized, pyrogen-free biological reactor, such as the "Microlift-15 liter sterilizable-in-place bioreactor with NBS Model ML-4100 control system" (New Brunswick Scientific Co., Edison, N.J.). This is a closed container with multiple entry sites for gases and liquids, ports for sampling, an agitator for stirring and temperature controls. The bioreactor is installed under an exhaust "fume hood." The hemoglobin is saturated with carbon monoxide (99.99% purity, Criogenic Rare Cas Co., Hanahan, S.C.) by sequential flushing with sterilized gas at 760 mm Hg, 4° C., with slow agitation. Total saturation is verified by use of a cooximeter (Model 282, Instrumentation Laboratories, Lexington, Mass.). The process takes approximately 15 minutes. The solution is left under CO at 760 mm Hg. Pasteurization is then carried out by gradually raising the temperature within the bioreactor from 4° to 60° C. and leaving it at that level for 9 hours, then raising it to 70° C. for 1 hour. After these intervals, the temperature is gradually lowered back to 4° C.

Example 4

Centrifugation with Chloroform

For this step, the Hb solution removed from the bioreactor is filtered through a 0.20 p filter into 250-ml sterile, pyrogen-free centrifuge bottles sealed with appropriate caps ("polyallomer" bottles resistant to chloroform, proteins and alcohol obtained from Sorvall Division, Du Pont Co., Wilmington, Del.).

A series of three centrifugations is carried out using a Sorvall centrifuge (Model 0TD75B with rotor TFA 20.250), in the following manner.

Centrifugation of Hb mixed with chloroform at a ratio of 15:1 (for each bottle: Hb,232 ml:chloroform, 18 ml) at 760×g and 4° C., for 30 minutes. The supernatant is passed into a second series of bottles using sterile pyrogen-free tubing and a peristaltic pump under laminar flow hood.

Centrifugation of Hb mixed with chloroform in the ratio 16:1 at 1,600×g and 4° C. for 15 minutes, and at 3,800×g for 15 minutes. The supernatant is transferred into a third series of bottles.

Centrifugation without chloroform at 61,400×g for 60 minutes.

After the third centrifugation, the Hb solution is transferred into 1000-ml sterile, pyrogen-free, evacuated bottles (Abbott Laboratories) with stirring bars. Remaining traces of chloroform are removed therefrom by flushing with a sterilized CO gas, with slow stirring at 4° C. for 2 hours.

The chloroform used for this step is HPLC grade with UV cutoff 244 nm (Fisher Scientific Co., Fair Lawn, N.J.). The bottles are reusable following treatment with (a) E-TOXA-Clean soap (Sigma Chemicals), (b) ethanol 190 proof, and (c) sterilization at 120° C. for 80 minutes.

This series of centrifugations not only removes all phospholipids, but also the non-heme proteins that denatured and precipitated in the previous step or pasteurization.

Example 5

Filtration Through Endotoxin Affinity-Chromatography Column

The Hb solution is passed through an affinity chromatography column, such as the Detoxi-Gel column (Pierce Chemical Co., Rockford, Ill.) using inlet and outlet "transfer packs" and a peristaltic pump, thus creating a closed system. The procedure is carried out under a Class 100 laminar flow hood.

By this step, the concentration of endotoxin can be reduced from 2.0–2.5 EU/ml to <0.10 EU/ml.

Example 6

Dialysis

The Hb solution is dialyzed in a ratio 1:10 against sterile, pyrogen-free, deionized water, adjusted to a pH of 7.20 by the addition of Tham solution. The dialysis is carried out by use of an artificial kidney with 6,000-dalton porosity, such as the "90 SCE—Artificial Kidney" (C-DAK Co., Miami Lakes, Fla.). This step eliminates small molecules, concentrates hemoglobin to 10 g/dl, and lowers the pH of the Hb solution from approximately 8.2 to approximately 7.2.

At this point in the process, "pure" hemoglobin has been produced, i.e., hemoglobin completely free of bacterial endotoxins, stromal lipids and phospholipids, and non heme proteins. Also, repeated filtrations through 0.20μ filters at various points in the process are expected to have eliminated all microbial contaminants, while pasteurization and chloroform treatment are expected to have inactivated both non lipid- and lipid-enveloped viruses. Furthermore, the use of hemoglobin in the carboxy- form allows its purification with a low degree of oxidation (1–2.5% met-hemoglobin formation).

Example 7

Modification of Hemoglobin

The reaction of hemoglobin with o-ATP, o-adenosine and reduced glutathione is carried out within the biological reactor as follows. Hemoglobin in the carboxy-state, 10 g/dl in water adjusted with Tham to a pH of 7.20, is reintroduced into tile bioreactor and kept at 4° C. with slow stirring under one atmosphere of carbon monoxide.

o-ATP is prepared according to Example 10 and stored in powder form. It is now dissolved into sterile, pyrogen-free water adjusted to a pH of 7.20, and immediately added to the Hb solution in a molar ratio, Hb:o-ATP 1:3. The reaction is allowed to proceed at 4° C. with 150 rpm stirring under CO for 24 hours. Samples of the solution are taken every 6 hours and examined by HPLC with a size-exclusion column to check the increase in molecular weight of hemoglobin and with an anionic-exchange column to check the change in electrical charge. A Waters HPLC system is used, which comprises a Waters 600 E Systems Controller, a Waters 712 injector, a Waters 990 Photodiode Detector and a NEC Power Mate 2 computer. The size-exclusion column (Protein Pak 300 SW) and the anionic-exchange column (DEAE-5 PW) are also obtained from Waters (Waters Chromatography Division, Millipore Co., Milford, Mass.). An ideal cross-linking condition occurs at about 24 hours, when examination by anionic-exchange HPLC reveals 90–95% of o-ATP to have been used in the chemical reaction. As a result thereof, a molecular aggregate is produced that consists of the following components shown in the Table.

TABLE

| Form | Hb Components MW (Kdaltons) | Percentage |
|---|---|---|
| Hemoglobin tetramers | 64 | 70 |
| Hemoglobin octamers | 130 | 21 |
| Hemoglobin dodecamers | 195 | 8 |

In other words, under the conditions of the reaction, o-ATP produces mostly intramolecular cross-linking, but also some intermolecular cross-linking. This, however, does not interfere with the following reaction.

After 24 hours, o-adenosine, prepared according to Example 11 and stored in powder form is dissolved into sterile water. pH 7.20 by the addition of Tham with a few drops of ethanol. This compound is added to the Hb solution in a molar ratio of Hb to o-adenosine of 1:5, and the reaction is allowed to continue under the same conditions for 24 hours. At this time, a second dose of o-adenosine is added in the same molar ratio of 1:5 and allowed to react for an additional 24 hours. Samples are examined by HPLC and the chemical reaction is quenched when the level of Hb tetramers has been reduced from 70 to 30%. If the reaction proceeds much beyond this point, polymers of excessive size are produced. GSH dissolved in water+Tham, pH 7.20, is then added to the Hb solution in a molar ratio Hb/GSH 1:20, and allowed to react for 16 hours. At this point, the hemoglobin molecular aggregate includes the following forms shown in the Table below.

TABLE

| Form of Hb | Hb Forms MW (Kdaltons) | Percentage |
|---|---|---|
| Tetramers | 64 | 30 |
| Tetramers × 2 | 130 | 20 |
| Tetramers × 3 | 195 | 20 |
| Tetramers × 4–6 | 256–390 | 30 |

This aggregate presents a single peak by HPLC-DEAE at 50–51 minutes.

At the end of these chemical reactions, hemoglobin is reconverted from the carboxy- to the oxy-form by repeated flushing with sterilized oxygen at 35 psi under gentle stirring at 4° C. plus exposure to 20-second pulses of strong light provided by a quartzline lamp, DWY 120 V 650 W (General Electric Co., Cleveland, Ohio) connected to a "type 4051 molequartz" (Mole-Richardson Co., Hollywood, Calif.). The reoxygenation of hemoglobin can be verified by the use of an IL cooximeter.

Example 8

Preparation of Composition of the Invention and Storage

In the final step, the Hb solution is dialyzed against 50 mM Tham solution pH 8.1 using an artificial kidney with a molecular weight cutoff of about 65–85 Kdalton ("Duo-Flux"; C-DAK, Miami Lakes, Fla.) until the percentage of Hb tetramers has been reduced from 30 to about 5%. The molecular size profile of the final Hb aggregate was as shown in the Table below.

TABLE

Molecular Size Profile of Hb Aggregates

| Form | MW (Kdaltons) | Percentage |
| --- | --- | --- |
| Hb tetramer | 64 | 5 |
| Hb tetramer × 2 | 130 | 18 |
| Hb tetramer × 3 | 195 | 20 |
| Hb tetramer × 4 | 260 | 30 |
| Hb tetramer × 5 | 325 | 16 |
| Hb tetramer × 6 | 390 | 10 |

Thus, the greatest percentage of molecular species is made of four Hb tetramers, with a molecular weight of 260,000 daltons. The aggregate presents a single peak by HPLC-DEAE at 50–51 minutes reflecting a change in isoelectric point from 6.8 to 6.1.

The dialysate containing discarded hemoglobin can be concentrated to Hb 10 g/dl by dialysis with a 6,000-dalton artificial kidney (90 SCE artificial kidney, C-DAK Co.) and reused for intermolecular cross-linking with o-adenosine. When the hemoglobin solution is to be used within hours or days, the first dialysis against 50 mM THAM solution may be followed by dialysis against an electrolyte-balanced saline solution (Normosol R, pH 7.4, containing 140 meq/l sodium, 5 meq/l potassium, 3 meq/l magnesium, 98 meq/l chloride, 27 meq/l acetate, and 23 meq/l gluconate; Abbott Laboratories).

Thus, in its final form, the present modified hemoglobin (Hb—PP—GSH) may be dissolved at a concentration of about 10 g/dl, either in water-THAM solution, pH about 8.1–8.2 to be stored for long periods of time, or in a balanced electrolyte solution, pH about 7.4 to be used without great delay.

As an example of the balanced electrolytes solution, magnesium chloride ($MgCl_2$), obtained from Matheson, Coleman and Bell, (Norwood, Ohio), is added to the solution in an amount equimolar with ATP. Mannitol, obtained from GIBCO-Dexter Co., Chagrin Falls, Ohio, is added in a dose of 2 mg/ml of solution.

For prolonged storage, Hb dissolved in water-THAM solution may be placed in 600-ml Fenwal plastic bags (sterile, pyrogen-free bags; Baxter Healthcare Co., Fenwal Division, Deerfield, Ill., and stored frozen at about −90° C. Under these conditions, no autoxidation of hemoglobin was found to occur for periods up to about one year. During this time, the polymerization profile of Hb, as determined by HPLC and isoelectric focusing, remained unchanged. For storage of intermediate duration, such as 1 to 6 months, hemoglobin dissolved in water-THAM solution may be stored in glass bottles (sterile, pyrogen-free "Empty evacuated container"; Abbott Laboratories), in liquid form, at about 4° C. Under these conditions, the autoxidation of Hb was found to occur at a rate of about 1% per month. Over a period of 6 months, the polymerization profile was found to change very little, with an about 5.–7% decrease in large polymers concomitant with an increase in octamers and tetramers.

For storage of short duration, e.g., less than 1 month, Hb may be dissolved in electrolyte-balanced solution and stored in glass bottles ("Empty evacuated container"; Abbott Laboratories), in liquid form, at 4° C. Under these conditions, the autoxidation of Hb was found to occur at a rate of about 3–5% per month.

Example 9
Characterization of the Composition of the Invention

The following procedures were used for the characterization of the new product. Hemoglobin, met-Hb and carboxy-Hb concentrations were measured on a cooximeter (Model 282 Cooximeter, Instrumentation Laboratories, Lexington, Mass.). Electrolyte concentrations and osmolarity of the solution were determined by means of an ASTRA apparatus (Beckman Co., Palo Alto, Calif.). Oncotic pressure was assessed by use of a Weil oncometer (Instrumentation Laboratories). Viscosity was determined at 37° C. and shear rate of 100/second, by use of a Brookfield viscometer (Brookfield Engineering Laboratories, Stoughton, Mass.).

The purity of Hb from other proteins, phospholipids and bacterial endotoxins was assessed as described above. Oxygen-binding capacity was calculated from the measurement of Hb concentration and oxygen volume content obtained on the cooximeter. Hb oxygen dissociation curves were obtained on a Hem-O-Scan apparatus (SLM Aminco, American Instruments, Silver Spring, Md.). $P_{50}$ values were read on these curves under standard conditions of temperature 37° C., pH 7.40, and $pCO_2$ 40 torr.

Analysis for phosphate content was carried out by the method of Fiske and Subbarow (Journal of Biological Chemistry, 66:375–380(1925)). Determination of GSH content was made according to the method of Reed et al. (*Analytical Biochemistry*, 106:55–62, (1980)).

Adenosine was determined by HPLC, with the absorbance being measured at 258 nm, and calculating the amount introduced and the amount incorporated into hemoglobin. (HD-PP-GSH)$_n$, where Hb=purified bovine hemoglobin, ATP was calculated from the determination of phosphate.

Figure 2:
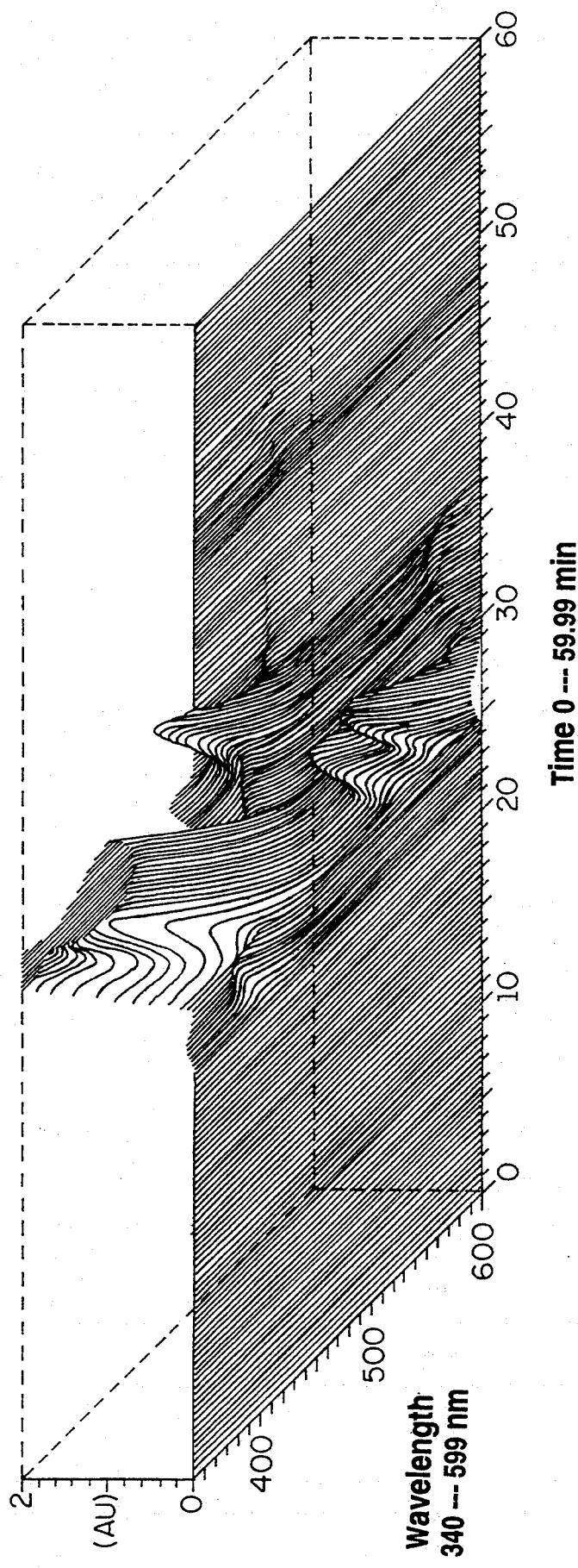
FIG. 2 shows a spectrum analysis of pure bovine hemoglobin obtained by HPLC with DEAE column. Chromatogram shows several peaks located between 20 and 36 minutes, corresponding to different isoelectric points of various Hb components.
Figure 3A:
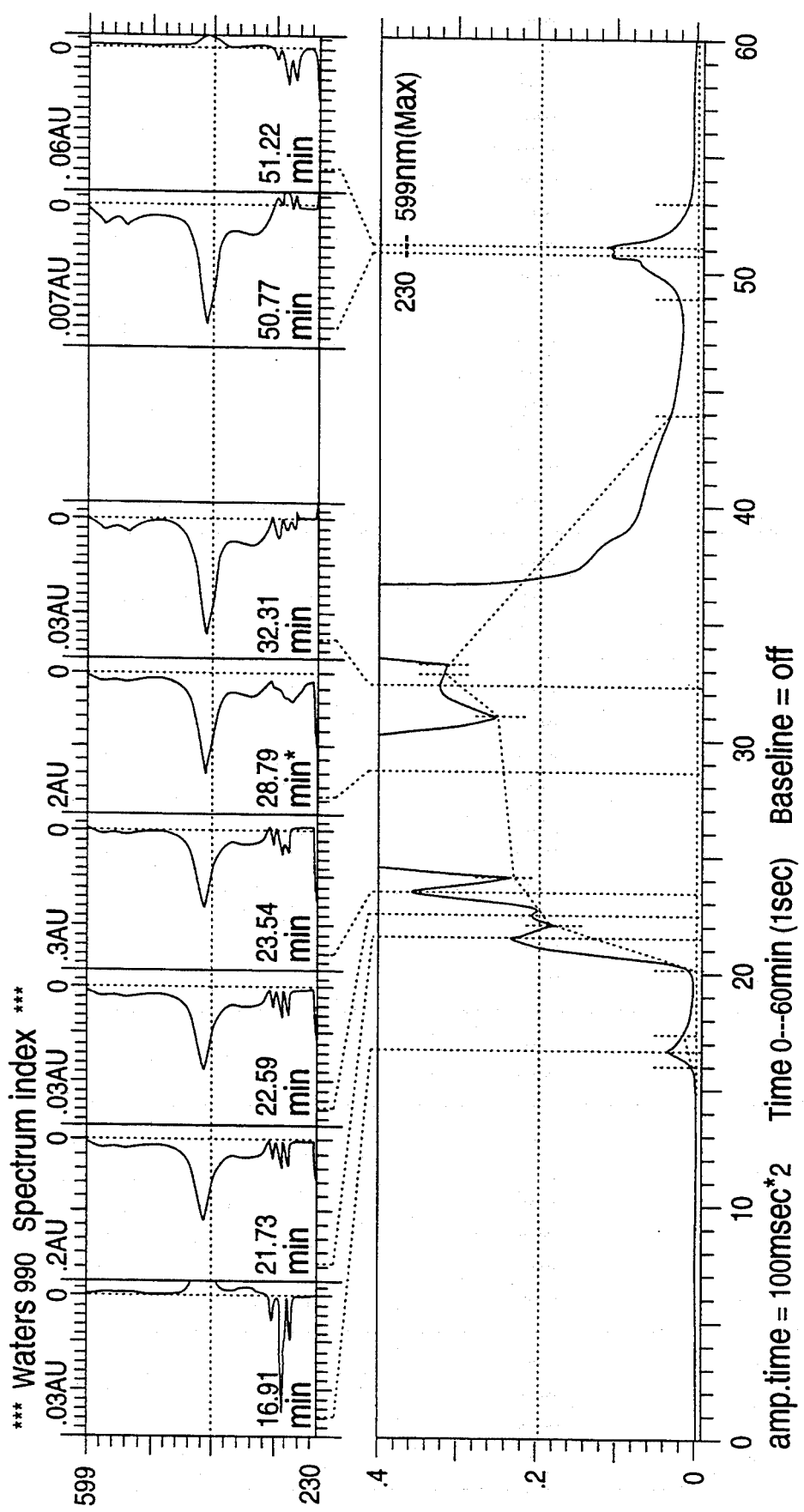
FIGS. 3A and 3B show the spectrum index of bovine hemoglobin before (3A) and after (3B) purification by pasteurization (HPLC with DEAE column, spectrum wavelength 230–599 nm).
Figure 3B:
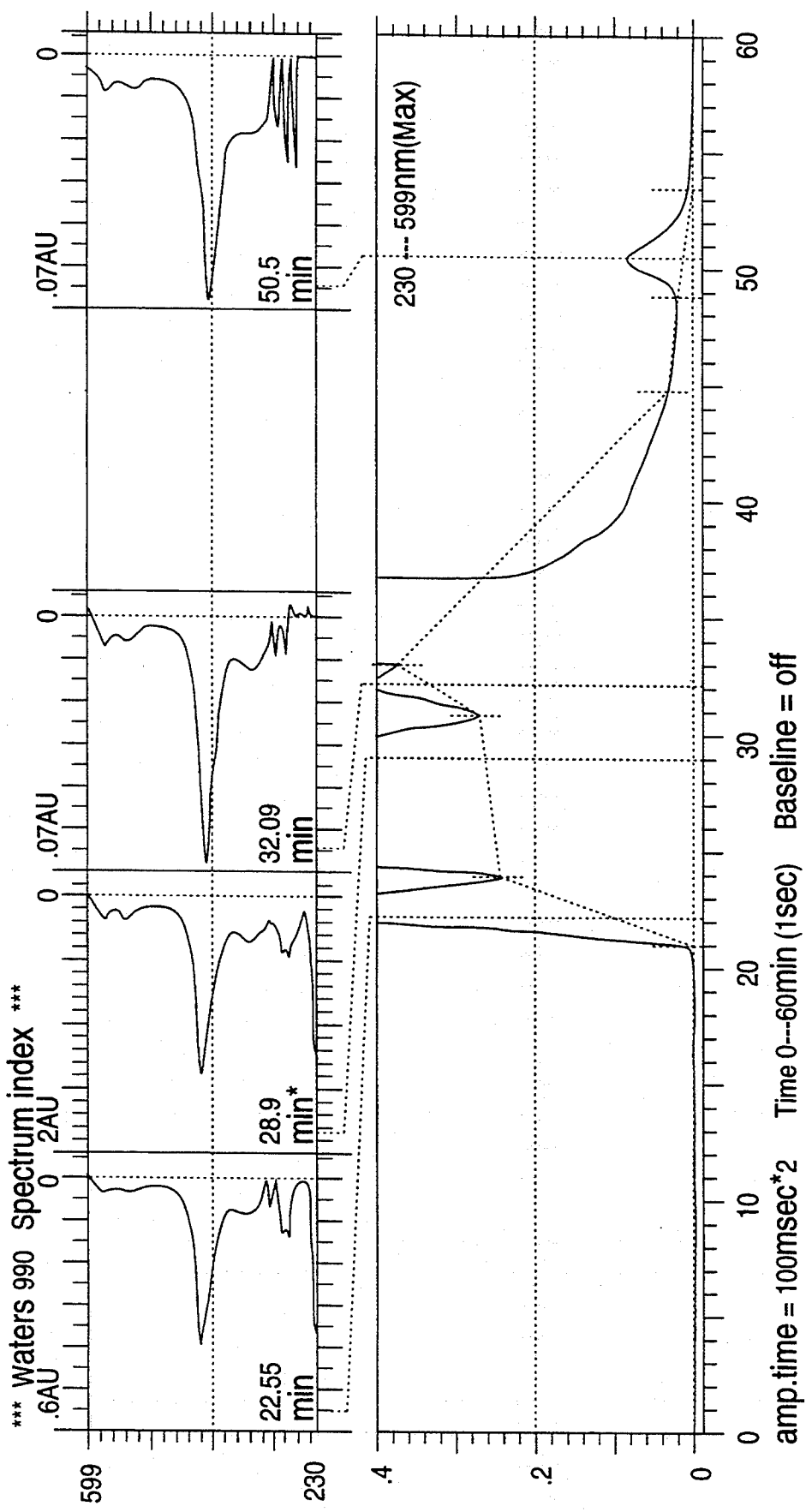
Figure 4:
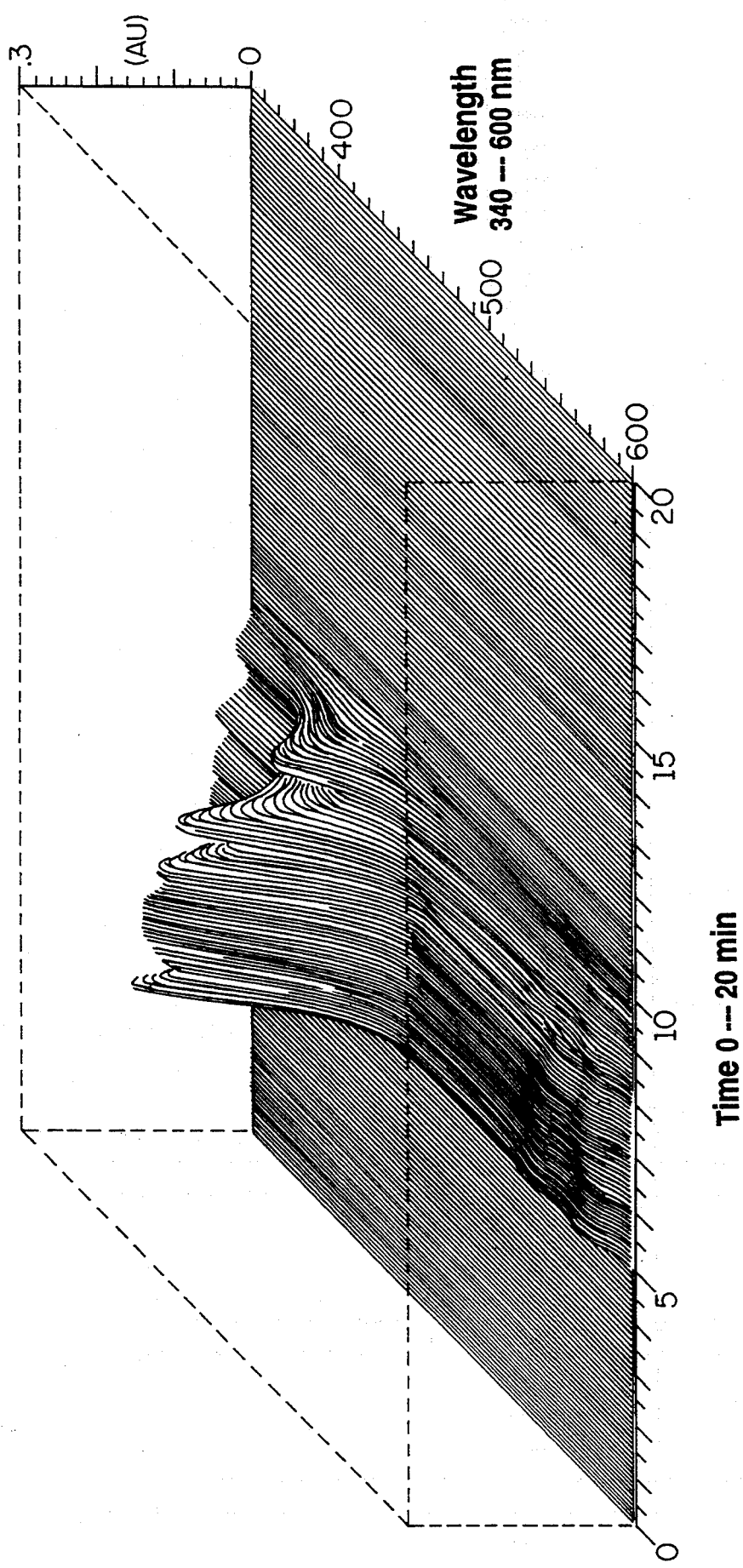
FIG. 4 shows a spectrum analysis by HPLC-size exclusion of bovine Hb cross-linked intramolecularly with o-ATP and intermolecularly with o-adenosine, and combined with reduced glutathione. The chromatogram shows a Hb molecular aggregate containing six peaks.
Figure 5:
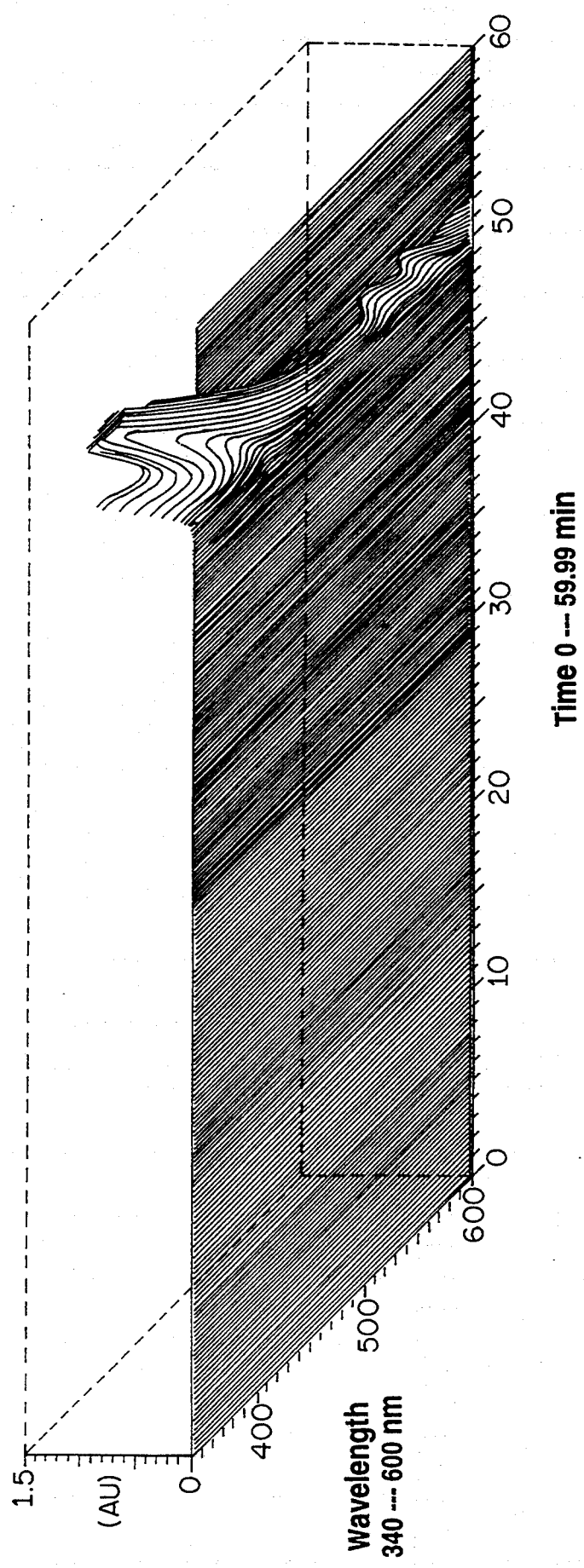
FIG. 5 shows s spectrum analysis by HPLC-DEAE column of bovine Hb modified as in FIG. 4. The chromatogram shows a single peak at retention time 51 minutes. The isoelectric point of Hb is shifted when compared to unmodified Hb due to an increase in electronegative surface charges.

The product here characterized was identified as (Hb—PP—GSH)$_n$, where Hb=purified bovine hemoglobin, PP=purine derivatives o-ATP and o-adenosine, and GSH=reduced glutathione. The basic molecule is Hb in tetrameric form, as shown in FIGS. 1 and 2. Its purification from other proteins is illustrated in FIG. 3. For each millimole (mM) of hemoglobin, the compound contains about 3 mM of ATP, about 10 mM adenosine and about 20 mM GSH. This chemical composition plus HPLC analysis conducted at various intervals during preparation indicate that o-ATP is primarily involved in the intramolecular cross-linking of Hb, while o-adenosine produces the intermolecular cross-linking. In addition, o-adenosine anchors the GSH molecule to Hb. The compound is illustrated in FIGS. 4 and 5. The spectrum analysis by HPLC-size exclusion shown in FIG. 4 reveals the compound to consist of the six molecular species shown in the Table below.

TABLE

Molecular Species of Hb

| Form | Percentage |
| --- | --- |
| 1. Hb (tetramer) | 5 |
| 2. (Hb)$_2$ | 18 |
| 3. (Hb)$_3$ | 20 |
| 4. (Hb)$_4$ | 30 |
| 5. (Hb)$_5$ | 16 |
| 6. (Hb)$_6$ | 10 |

Among these, (Hb)$_4$, i.e., the aggregate of four tetramers, appears to be the predominant species. Analysis by HPLC-DEAE column (FIG. 5) reveals a single peak at 50–51 minutes, indicating the compound to possess a uniform, reduced (with respect to unmodified Hb) isoelectric point. Analysis by isoelectric focusing (IEF) (FIG. 6) shows these modifications of Hb from another perspective.

When the compound (Hb—PP—GSH) is stored in a water-THAM solution, the following electrolytes may be added before use.

| | |
|---|---|
| Sodium Chloride, e.g., 25 meq/ml Inj. USP NaCl (Abbott Lab.) | 113 meq/l |
| Sodium Bicarbonate, e.g., 1.0 meq/ml Inj. USP NaHCO$_3$ (Abbott Lab.) | 27 meq/l |
| Potassium Chloride, e.g., 20 meq/ml Inj. USP KCl (Abbott Lab.) | 4 meq/l |
| Calcium Gluconate, e.g., 0.465 meq/ml Inj. USP (American Regent Lab.) | 5 meq/l |
| Magnesium Sulfate, e.g., 0.8 meq/ml Inj. USP MgSO$_4$ (ANTRA Pharmaceutical) | 3.5 meq/l |

In addition, mannitol may be added in an amount of about of 0.8 mg/ml solution. With these solutions, the final hemoglobin solution may have tile composition shown in the following table.

TABLE

Characteristics of Hemoglobin Solution (Final Product)

| Solution Component | Amount |
|---|---|
| Hemoglobin, gm/dl | 10.0 |
| Met-Hb (% of hemoglobin) | 3.5 ± 0.05 |
| Carboxy-Hb (% of hemoglobin) | 1.5 ± 0.05 |
| pH, Units | 7.4 ± 0.05 |
| THAM sol. ml/dl | 6.66 |
| Sodium, meq/l | 140 |
| Potassium, meq/l | 4 |
| Calcium, meq/l | 5 |
| Magnesium, meq/l | 3.5 |
| Chloride, meq/l | 117 |
| Bicarbonate, meq/l | 27 |
| Gluconate, meq/l | 5 |
| Sulfate, meq/l | 3.5 |
| Mannitol, mg/dL | 80 |
| Colloid-osmotic pressure, mm Hg | 22 ± 2 |
| Viscosity, cP | 1.74 ± 0.04 |
| Osmolarity, mOsm/l | 325 ± 10 |
| Non-Hb Proteins | undetectable |
| Stromal phospholipids and lipids | undetectable |
| Bacterial endotoxins | <0.10 EU/ml |
| Sterility | sterile |
| Stability at −90° C. | indefinite |

When the compound (Hb—PP—GSH) is stored dissolved in Normosol R, only Mannitol is added before use, in the same dose as above. The characteristics of this final product are similar to those shown in the previous table, with the exception that Normosol R does not contain any calcium gluconate.

At the concentration of 10 g/dl, this Hb solution exposed to atmospheric air transports 13 volumes per cent of oxygen, which indicates an oxygen-binding capacity close to 100% ( 1.3 volumes of oxygen per 1 gm of Hb) . The P$_{50}$ value of the solution is high (∼28 mm Hg) despite polymerization due to the high concentration of chloride. The osmolarity is higher than that of plasma, but the viscosity is lower than that of whole blood. The colloid-osmotic pressure is lower than that of plasma despite the high concentration of hemoglobin (compared to albumin), due to the fact that hemoglobin is polymerized, so that the number of "Hb particles" is reduced.

Example 10

Large-Scale Preparation of o-ATP

The basic method of preparation of o-ATP is known to the art (see: S. B. Easterbrook-Smith et al., "Pyruvate Carboxylase:Affinity labeling of the magnesium adenosine triphosphate binding site," European Journal of Biochemistry, 62: 125–130 (1976).

Modifications were made to produce larger quantities of material and assure a satisfactory chemical reaction with hemoglobin.

Figure 7:
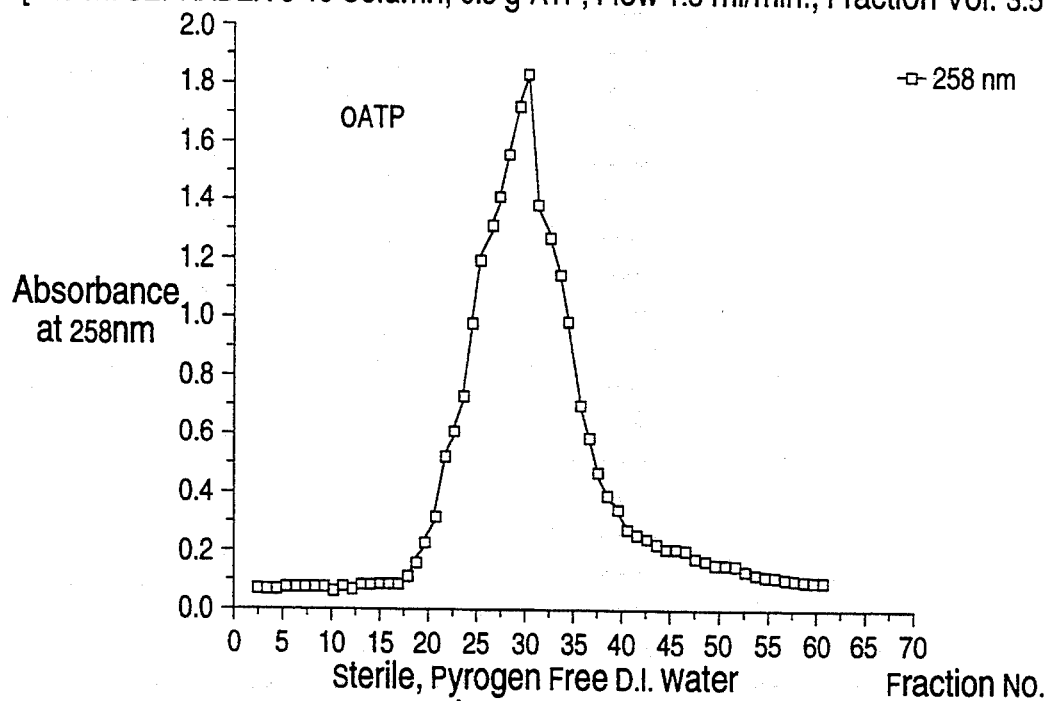
FIG. 7 shows the 258 nm absorbance of successive fractions of the o-ATP and sodium periodate reaction mixture eluted from a Sephadex column with water.

Adenosine 5'-triphosphate disodium salt hydrate (ATP), F. W. 551.15, and sodium periodate (NaIO$_4$) 99% purity, F. W. 213.89, were obtained from Aldrich Chemical Company, Milwaukee, Wis. Ten 120-ml Sephadex G-10 columns were obtained from Pharmacia Fine Chemicals, Piscataway, N.J. For each column, 550 mg of ATP were dissolved in 15 ml of sterile pyrogen-free water (water for injection, Abbott Laboratories), adjusted with Tham solution to a pH of 7.0, at 0° C. Sodium periodate was added in a molar ratio (ATP/NaIO$_4$) of 1:1.1, and the solution was allowed to stand at 4° C. in the dark for one hour. The reaction was stopped by the addition of ethylene glycol in a molar ratio (ATP/ethylene glycol) 2:1 for 15 minutes. The reaction mixture was loaded onto the Sephadex G-10 column previously equilibrated with "water for injection," at 4° C. The column was eluted with 200 ml of water. The leading half of the nucleotide peak, fractions 20 to 30, as shown in FIG. 7, was pooled and immediately lyophilized with a Labconco Freeze-Dry System with Stoppering Tray Dryer (Labconco Co., Kansas City, Mo.) with vacuum <10μ Hg, at −40° C. The powder was stored in dark bottles at −90° C. until use.

The concentration of o-ATP is determined by measuring absorbance at 258 nm, while the presence of periodate is assessed by measuring absorbance at 232 nm. The columns are washed with water for injection for 30 hours at 4° C., until the eluate presents less than 0.043 absorbance at 232 nm, i.e., until all periodate has been washed out, before reuse.

Two measures are important for the purpose of this invention: (1) that only fractions containing o-ATP without any trace of periodate be collected; and (2) that these fractions be immediately lyophilized and frozen at −90° C. These measures will prevent the oxidation of hemoglobin upon chemical reaction.

Example 11

Large-Scale Preparation of o-Adenosine

The basic method of preparation of o-adenosine is known to the art (Khym, J. X., and Cohn, W. E., "Characterizations and some chemical reactions of periodate-oxidized nucleotides," Journal of American Chemical Society 82:6380–6386(1960)). Modifications were made to produce larger quantities of material and to assure a satisfactory chemical reaction with hemoglobin.

Figure 8:
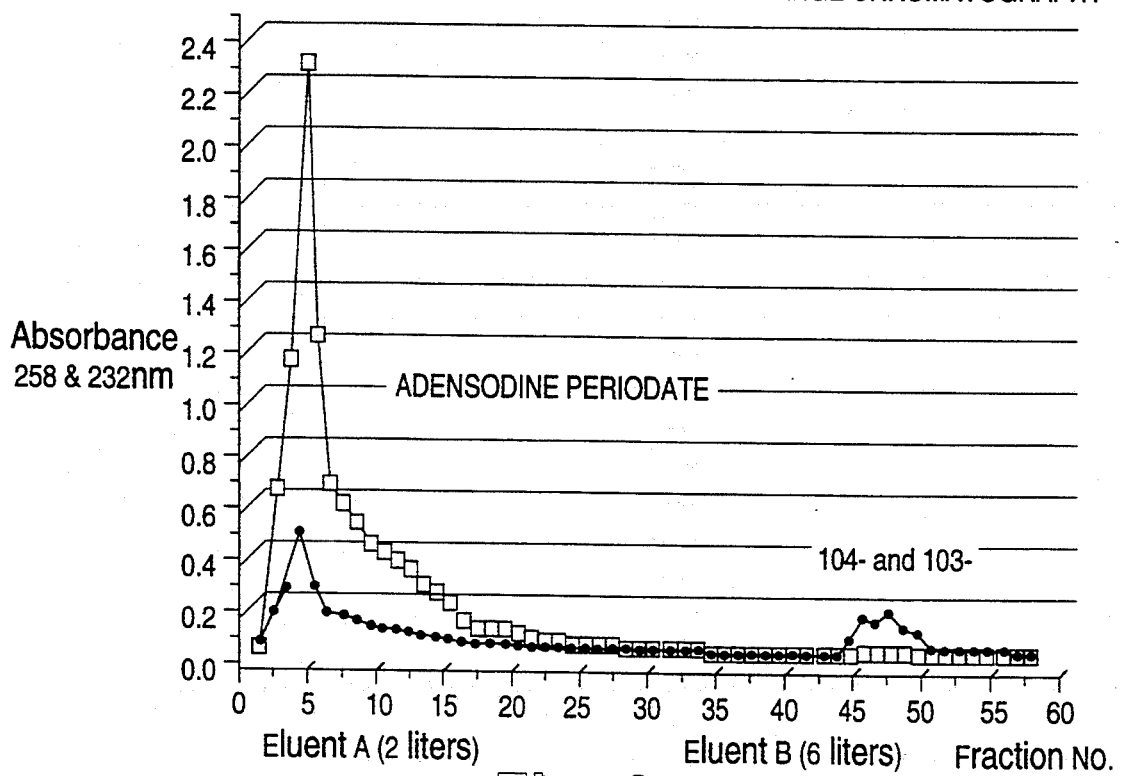
FIG. 8 shows the 258 nm and 232 nm absorbances of successive fractions of the o-adenosine and sodium periodate reaction mixture eluted from an anion exchange column with Eluate A.

Adenosine 98% purity was obtained from Sigma Chemical Co., while sodium periodate was obtained from Aldrich Chemical Co. Adenosine, 6 g, was dissolved in 200 ml of 150 mM NaIO$_4$ in water, at room temperature, for 30 minutes. The solution was passed through a 300-ml column of anion exchange resin AG 1-X-8, 100–200 mesh acetate form (Bio-Rad Laboratories, Richmond, Calif.) previously equilibrated with 20 mM acetic acid (Eluate A) obtained from Fisher Scientific Co. The column was eluted with two liters of Eluate A, at the flow rate of 15 ml/minute, temperature 4° C., obtaining fractions of 150 ml. Only factions 2 to 15 were collected (as shown in FIG. 8), which were immediately lyophilized and frozen, as done for o-ATP.

Before reuse, six liters of 100 mM ammonium chloride (Eluate B) were applied to the column in order to release all periodate. The concentration of periodate in the fractions was determined by measuring absorbance at 232 nm. After this, the column was washed with six liters of "water for injection" and then equilibrated again with 20 mM acetic acid.

Two measures are important for the purpose of this invention that only only fractions containing o-adenosine without any trace of periodate be collected, and that these fractions be immediately lyophilized and frozen at −90° C. These measures will prevent the oxidation of hemoglobin upon chemical reaction.

DESCRIPTION OF APPLICATIONS OF THE INVENTION

Example 12

Toxicity in Rabbits

The toxicity of the composition of this invention (Hb—PP—GSH) was tested in rabbits according to a method previously reported in the scientific literature (Feola, M., et al., "Toxicity of Polymerized Hemoglobin Solutions", Surgery, Gynecology and Obstetrics 166:211–222(1988)).

Twelve New Zealand rabbits of 4.0 Kg body weight had sterile cannulae inserted under local anesthesia with 1% lidocaine into the central artery of one ear and the marglobal vein of the other ear. A sterile catheter was inserted into the urinary bladder. A thermistor probe and ECG needle-electrodes were inserted under local anesthesia in time limbs. Electrocardiogram (EGG), blood pressure, body temperature, and urinary output were continuously monitored for three hours, after which catheters and electrodes were removed and the animals were returned to their cages. After 30 minutes of steady state (baseline), 80 ml of blood, corresponding to ⅓ of blood volume (calculated blood volume in the rabbit=6% of body weight in Kg) were removed from the arterial line over a period of 5 minutes. An equal volume of Hb—PP—GSH dissolved in an electrolyte solution was infused through the venous line over a period of 30 minutes. This was equal to approximately 2 grams of hemoglobin. The removal of blood caused a drop in blood pressure with an increase in heart rate. These changes were quickly corrected. Moreover, the pulse pressure (difference between systolic and diastolic pressure), which became narrow after the hemorrhage, first returned to normal, then became greater than at baseline, indicating a vasodilator effect of the Hb solution. This effect lasted the entire acute period of observation of three hours. The ECG showed no cardiac arrhythmia. The urinary output remained normal without any extravasation of hemoglobin into the urine.

Blood samples taken 30 mixtures, 1, 3, and 24 hours after blood replacement revealed the following.

(1) No reduction of white blood cells and platelets in excess of tile hemodiluting effect.

(2) No activation of intravascular coagulation and fibrinolysis, as determined by measurement of serum fibrinogen, prothrombin time and fibrin split products.

(3) No elevation of creatine phosphokinase brain isoenzyme (CPK-BB) or myocardial isoenzyme (CPK-MB) that would suggest cerebral or myocardial damage.

(4) No elevation of serum glutamic pyruvic transaminase (SGPT) suggestive of liver injury;

(5) Normal arterial blood gases indicative of normal pulmonary function.

(6) Normal serum creatinine suggestive of normal renal function.

Combined blood and urine samples at 3 and 24 hours revealed normal creatinine clearance, again indicative of normal renal function. Whole blood oxygen dissociation curves showed no change in $P_{50}$ value, i.e., no increase in oxygen affinity due to hemoglobin. The level of plasma Hb at 24 hours was approximately 50% of the initial level, suggesting a hemoglobin half-life of 24 hours.

The animals appeared and behaved normally for 24 hours. At this time, they were killed and the vital organs were examined histologically. None of the pathological changes previously reported in the scientific literature were found in (a) heart, (b) lungs, (c) liver and (d) kidneys. These findings contrast sharply with those previously reported (see reference above) following the use of non-pure hemoglobin cross-linked with glutaraldehyde.

Example 13

Efficacy in Rabbits

The efficacy of the product as a blood substitute was tested in rabbits. Following instrumentation similar to that described in the previous example, a control group of 10 New Zealand rabbits of 4.0 Kg body weight were subjected to the removal of ⅓ of calculated blood volume (blood volume=6% of body weight in Kg), followed by the removal of another ⅓ after 15 minutes. Without treatment, all of these animals died within one hour. An experimental group of 10 rabbits was subjected to the same procedure, but receives an infusion of Hb—PP—GSH dissolved in an electrolyte solution in the same volume as the total blood loss. All of these animals survived and reconstituted their baseline hematocrit (concentration of red blood cells) within seven days.

Example 14

Vasodilation After Blood Replacement in Rats

Twelve Sprague-Dawley rats weighing 350–450 gm were anesthetized by intraperitoneal injection of sodium pentobarbital, 45 mg/Kg, and placed on a surgical board in the supine position. The right femoral artery, carotid artery and external jugular vein were surgically exposed and cannulated with polyethylene catheters (model PE 50; Intramedic, New York). The external jugular catheter was advanced into the right atrium, while a thermistor probe (model IF, Columbus Instruments, Columbus, Ohio) was advanced through the carotid artery into the ascending aorta. Each of the catheters was filled with saline solution containing bovine heparin 5 IU/ml. The femoral arterial and the jugular venous lines were connected to pressure transducers. Needle electrodes were inserted subcutaneously into the limbs and used to monitor the electrocardiogram (ECG). Heating lamps were adjusted to maintain constant body temperature. heart rate was determined from the ECG tracing, cardiac output was measured by thermodilution, by injecting 200 μl of saline solution maintained at room temperature (20°-22° C.) into the right atrium and recording a thermodilution curve from the aortic thermistor. Systemic vascular resistance was calculated as the mean arterial pressure minus the right atrial pressure divided by the cardiac output.

Following recording of baseline hemodynamic data, ⅓ of calculated blood volume (blood volume in the rat=7% of body weight in Kg) was removed from the arterial line over a 5-minute period. After 15 minutes, Hb—PP—GSH dissolved in an electrolyte solution in the same volume, was infused through the venous line. Heart rate, mean arterial pressure, and cardiac output were measured and systemic vascular resistance was calculated at baseline ($T_1$) 15 minutes after blood removal ($T_2$) and 15 minutes after hemoglobin infusion ($T_3$). Statistical analysis of tile data was carried out using Student's t-test for paired data.

The results, summarized below, show increased systemic vascular resistance after blood removal, followed by reduction to normal and by vasodilation, even with respect to baseline, after blood replacement.

TABLE

| | Hemodynamic Profiles after Blood Replacement with Hb-PP-GSH | | |
|---|---|---|---|
| | Baseline | Hemorrhage | Hemoglobin |
| Heart Rate beats/minute) | 320 ± 5 | 390 ± 10* | 300 ± 10* |
| Mean Arterial Pressure (mm Hg) | 105 ± 5 | 90 ± 3* | 105 ± 5* |
| Cardiac Output (ml/Kg/minute) | 425 ± 20 | 275 ± 15* | 455 ± 28* |
| Systemic Vascular Resistance (mm Hg/ml Kg/minute) | 0.23 ± 0.02 | 0.33 ± 0.03* | 0.21 ± 0.02* |

Numbers = Mean ± Standard Deviation
*Statistically significant difference (P < 0.05) from previous time interval.

Example 15

Generation of Oxygen Free-Radicals in Rabbits

Twelve New Zealand rabbits of 4.0 Kg body weight were sedated with chlorpromazine (5 mg/Kg, intramuscularly) and subjected to limited instrumentation. Sterile plastic cannulae were inserted into the central artery and the marginal vein of one ear, and a thermistor probe and needle electrodes were inserted subcutaneously into the limbs. One-third of calculated blood volume (2% of body weight in Kg) was removed from the arterial line over a period of five minutes and the same volume of Hb solution was infused through the vein over a period of 30 minutes. One control group of six rabbits received unmodified Hb, while the experimental group (six rabbits) received Hb—PP—GSH dissolved in an electrolyte solution. The effects were studied in terms of plasma levels of hydrogen peroxide ($H_2O_2$) and lipid peroxides, determined at baseline, and 15 minutes, 1 hour, 3 hours and 24 hours after Hb infusion. Plasma Hb and met-Hb were also measured at the same time intervals.

$H_2O_2$ increased in the group receiving unmodified Hb from 2±2 to 70±5 micromoles/milliliter after one hour, then decreased to 50±5 $\mu$mol/ml at three hours and to 10±5 $\mu$mol/ml at 24 hours. In the experimental group, $H_2O_2$ increased only from 2±2 to 10±2 $\mu$mol/ml at one hour, and returned to baseline after three hours. Similarly, lipid peroxides increased from 1.5±0.9 mamomoles/milliliter at baseline to 4.0±1.0 nmol/ml after one hour in the control group. No significant increase occurred in the experimental group.

Plasma met-Hb increased fro 0 to 15% in one hour in the group that received unmodified Hb. It increased fro 0 to 5% in the group that received Hb—PP—GSH. The difference in these variables between the two groups was found significant by statistical analysis, Student's t-tests for unpaired and paired samples plus ANOVA.

Although the invention has been described in conjunction with the foregoing specific embodiment, many alternatives, variations and modifications will be apparent to those of ordinary skill in the art. Those alternatives, variations and modifications are intended to fall within the spirit and scope of the appended claims.

Example 16

Formulation of Hb—PP—GSH in the Absence of Electrolytes

The preparation of Hb—PP—GSH was carried out as shown in Examples 1 to 9. The modified hemoglobin was dialyzed solely against a 50 mM Tham solution (Tromethamine, Injectable, Abbott Laboratories, N. Chicago, Ill.), pH 8.1. In its final form, the Hb—PP—GSH preparation was left in water plus Tham solution, pH 8.1, at a concentration of 10 g/dl. The formulation lacked electrolytes, but contained mannitol which was added as previously, at a dose of 0.8 mg/ml of solution. Typically, the solution contained 6.66 ml of Tham for each 100 ml of water.

Example 17

Characteristics of the Hb—PP—GSH Preparation Lacking Electrolytes

In vitro observation showed that Hb—PP—GSH may be preserved in the refrigerator, at 4° C., for longer periods of time when dissolved in a non-electrolytic solution such as Tham solution than when dissolved in a saline solution.

It was observed that over a period of 3 months the autoxidation of hemoglobin to met-Hb occurred at a rate of 3-5% per month with the formulation containing electrolytes whereas it occured at a rate of 1% per month with the solution without electrolytes. This can be explained on the basis that chloride ions, that are present in the saline solution, reduce the oxygen-affinity of hemoglobin, facilitating oxygen release and autoxidation.

Example 18

In vivo Effect of Non-Electrolytic Hb—PP—GSH

The Hb—PP—GSH was left dissolved in Tham solution at a concentration of 10%. Mannitol was added in an amount of 0.8 mg/ml, but electrolytes were not added. A volume equal to one third of the calculated blood volume was injected intravenously over a period of 30 minutes to a group of 9 rats (350–400 g body weight). The animals had normal access to food and water before the experiment and were anesthetized by intraperitoneal injection of sodium pentobarbital, 45 mg/Kg, and handled as reported in Example 14 above.

Body temperature, respiration, electrocardiogram, arterial blood pressure and cardiac output were monitored for a period of 2 hours. Urinary output was recorded for one hour before, and two hours after, the administration of the hemoglobin solution, and the urine was checked for hemoglobinuria. Blood samples were taken before, and at 15-minute intervals for 2 hours, after the administration of Hb—PP—GSH for tile measurement of ionized and total calcium levels in serum.

None of the animals developed any sign of acute toxicity. A transient decrease in heart rate occurred, but without arrhythmias or change in electrocardiogram patterns. The respiratory rate, blood pressure and cardiac output remained significantly constant. The urinary output of the animals increased from about $0.6\pm0.3$ ml/hour to about $1.6\pm0.3$ ml/hour (P less than 0.05), and there was no hemoglobinuria. Total serum calcium remained substantially constant whereas ionized calcium decreased from about $0.85\pm0.05$ to about $0.62\pm0.03$ mM. This, however, was not statistically significant and lasted only a few minutes. The change in ionized calcium level was reversed by the intravenous administration of calcium gluconate (10% calcium gluconate for injection, W. A. Butler, Cincinnati, Ohio) infused at the dose of 2 mg of calcium/100 g body weight over a 2 minute interval.

This experiment proves that Hb—GSH may be administered even without the addition of electrolytes, e.g., when the volume to be infused corresponds to less than one third of the calculated blood volume.

Example 19

Clinical Testing of Hb—PP—GSH

Hb—PP—GSH was tested in humans, in Kinshasa, Republic of Zaire, Africa, after approval from the Department of Education and Scientific Research of that Government. During the period of Aug. 15 and Sep. 15, 1990, a group of 9 patients was treated at the Center for Sickle Cell Anemia in Kinshasa. There were 5 males and 4 females, 4–13 years of age. Five of the children presented severe anemia, with blood hemoglobin levels of 5 g/dL or less. Four of the children had a lesser degree of anemia, with hemoglobin levels about 8 g/dL, but were suffering from a "sickle cell crisis", i.e., acute microvascular blockage in the hands and feet (2 patients), in the left lung (1 patient), and in the spleen (1 patient). The patients presented pain, fever and generalized malaise and weakness.

The group of patients with severe anemia was medically judged in need of a blood transfusion whereas the second group was to be treated with intravenous fluids, vasodilators and analgesic anti-inflammatory agents. Hemoglobin (Hb—PP—GSH) was considered indicated for treatment of both groups. Hemoglobin was expected to provide a substitute for red blood cells (RBCs) and to improve the circulation and tissue oxygenation by the following two mechanisms.

Increased in circulating blood volume.

Increased delivery of oxygen.

In addition, since the hemoglobin is cross-linked with derivatives of ATP that is a vasodilator and adenosine that is also a vasodilator and an anti-inflammatory agent, the solution was expected to alleviate any microvascular blockage afflicting the patients with a "sickling" crisis.

As a further advantage over a blood transfusion, a treatment with the Hb—PP—GSH solution of the invention carries no risk of blood-transmissible diseases such as malaria, bacterial diseases, and AIDS.

The Hb—PP—GSH of this invention was stored in Fenwal bags, each containing 250 ml of 10% hemoglobin in a water-THAM solution. The bags were maintained in the frozen state (packed in gel ice) until use. Two hours before administration, the Fenwal bags were exposed to room temperature and the hemoglobin solution thawed. Electrolytes and mannitol were added as described above. Tile entire volume of each bag was given intravenously at the rate of about 30 drops per minute. This volume corresponds to about 12–23% blood volume, calculated for each patient as 7% of body weight in kilograms.

One patient with severe anemia, hemoglobin 3.5 g/dl, received two infusions on two consecutive days.

The vital signs temperature pulse respiration and blood pressure, were taken every 15 minutes during the administration of hemoglobin and for 2 hours thereafter. During this period, attention was also focused on the possible development of allergic reactions such as urticaria, skin rashes, bronchospasm, and nausea-vomiting. Urinary output was measured for a two-hour period before and a two-hour period after the administration of Hb—PP—GSH. The urine was tested for the presence of hemoglobin, and the sediment was examined microscopically. Blood samples were taken before, soon after Hb—PP—GSH administration, two hours thereafter, and daily for 5 days. The patient's blood was tested for plasma hemoglobin (the hemoglobin infused), total hemoglobin (hemoglobin infused plus that contained in RBCs) and for reticulocytes (young RBCs).

None of the patients developed an allergic reaction, and all felt generally improved. Those with "sickling" crisis reported a lessening of the pain without use of analgesics. The fever abated, the pulse became less rapid, the blood pressure remained stable with some increase in pulse pressure indicative of vasodilation, and the respiration was unchanged. The urinary output increased for the whole group from a mean value of about $50\pm7$ ml/two hours before administration of Hb—PP—GSH to about $130\pm15$ ml two hours after administration of Hb—PP—GSH. The urine showed no hemoglobinuria and no casts were found in the sediment. The most impressive finding was represented by a progressive improvement in total hemoglobin over a period of 5 days from a mean value for the entire group of about $6.39\pm2.12$ to about $10.5\pm1.13$ g/dl and a significant increase in reticulocytes from about $11.2\pm7.6$ to about $44.2\pm12/100$.

This suggests that the hemoglobin solution not only provided an immediate substitute for RBCs, but stimulated the patients' bone marrow to produce new RBCs of their own. This stimulation was solely documented for 5 days but probably lasted longer than that.

In conclusion, the administration of Hb—PP—GSB in significant volumes to 9 children suffering from sickle cell anemia produced no toxic or allergic reactions, improved their general condition and had a protracted beneficial effect on the bone marrow with the production of new red blood cells.

The invention now being fully described, it will be apparent to one of ordinary skilled in the art that many changes and modifications can be made thereto with departing from the spirit or scope of the invention as set forth herein.

It is claimed:

1. A method of treating a human in need of blood comprising intravenously administering to the human an effective amount of a blood substitute comprising substantially pyrogen-free, microbe-free, active hemoglobin reacted with o-ATP and o-adenosine to form a cross-linked hemoglobin.

2. The method of claim 1, wherein the blood substitute further comprises a pharmaceutically-acceptable aqueous solution.

3. The method of claim 1, wherein
the blood substitute is free of electrolytes.

4. The method of claim 1, wherein
the human is afflicted by acute blood loss.

5. The method of claim 1, wherein
the human is afflicted with a sickling crisis of sickle cell anemia.

6. A method of restoring lost blood volume of a human comprising intravenously administering to the human an effective amount of a blood substitute comprising substantially pyrogen-free, microbe-free, active hemoglobin reacted with o-ATP and o-adenosine to form a cross-linked hemoglobin.

7. The method of claim 6, wherein
the blood substitute is free of electrolytes.

8. The method of claim 6, wherein the blood substitute further comprises
a pharmaceutically-acceptable aqueous solution.

9. The method of claim 6, wherein
the human is affected with a sickling crisis.

10. A method of treating a human afflicted with a sickling crisis of sickle cell anemia comprising intravenously administering to the human an effective amount of a blood substitute prepared by a method comprising
converting hemoglobin in solution to carboxy-hemoglobin;
pasteurizing the carboxy-hemoglobin solution to denature and precipitate non-heme proteins;
removing phospholipids and precipitated non-heme proteins from the carboxy-hemoglobin solution;
removing endotoxins from the carboxy-hemoglobin solution;
concentrating the carboxy-hemoglobin solution;
predominantly intramolecularly cross-linking the carboxy-hemoglobin in the concentrated carboxy-hemoglobin solution with o-ATP;
predominantly intermolecularly cross-linking the carboxy-hemoglobin with o-adenosine;
adding glutathione to the cross-linking carboxy-hemoglobin solution to quench the o-adenosine cross-linking reaction;
converting the cross-linked carboxy-hemoglobin in the cross-linked carboxy-hemoglobin solution to cross-linked oxy-hemoglobin; and
forming an aqueous solution of the cross-linked oxy-hemoglobin.

11. The method of claim 10, wherein
the aqueous solution of cross-linked oxy-hemoglobin is a pharmaceutically-acceptable electrolyte-free solution.

12. A composition for use as a blood substitute, comprising substantially pyrogen-free, microbe-free, active hemoglobin reacted with o-ATP and o-adenosine to form a cross-linked hemoglobin.

13. The composition of claim 12, in the form of a solution wherein the solution further comprises magnesium chloride at a concentration about equimolar with the o-ATP.

14. The composition of claim 12, wherein the o-ATP comprises periodate-oxidized ATP and the o-adenosine comprises periodate-oxidized adenosine; and
the substantially pyrogen-free, microbe-free, active hemoglobin is intramolecularly cross-linked with the periodate-oxidized ATP and intermolecularly cross-linked with the periodate-oxidized adenosine to form polyhemoglobin.

15. The composition of claim 12, further comprising reduced glutathione.

16. The composition of claim 12, wherein the cross-linked hemo-globin has a molecular weight of about 130,000 to 390,000.

17. The composition of claim 12, wherein less than 5% of the substantially pyrogen-free, microbe-free, active hemoglobin comprises met-hemoglobin.

18. The composition of claim 12, wherein the substantially pyrogen-free, microbe-free, active hemoglobin comprises bovine hemoglobin.

19. The composition of claim 12, prepared by a method comprising separating whole blood into a leukocyte-erythrocyte mixture, platelets and plasma and suspending the thus obtained mixture in an aqueous solution;
cooling the aqueous solution comprising the leukocyte-erythrocyte mixture to aggregate the leukocytes and removing the leukocyte aggregate to obtain a substantially leukocyte-free solution;
dialyzing the substantially leukocyte-free solution against a hypotonic solution to extract hemoglobin from erythrocytes in the substantially leukocyte-free solution and separating out the erythrocytes from the extracted hemoglobin in the substantially leukocyte-free solution by ultrafiltration under increased hydrostatic pressure to obtain an extracted hemoglobin solution;
converting the extracted hemoglobin in the extracted hemoglobin solution to carboxy.-hemoglobin to obtain a carboxy-hemoglobin solution;
pasteurizing the carboxy-hemoglobin solution to denature and precipitate non-heme proteins;
removing phospholipids and precipitated non-heme proteins from the carboxy-hemoglobin solution;
removing endotoxins from the carboxy-hemoglobin solution by affinity chromatography;
concentrating the carboxy-hemoglobin in the carboxy-hemoglobin solution to a concentration of about 10 g/dl to obtain a concentrated carboxy-hemoglobin solution;
reacting the carboxy-hemoglobin in the concentrated carboxy-hemoglobin solution with o-ATP to effect predominantly intramolecular cross-linking of carboxy-hemoglobin, thus obtaining an intramolecularly cross-linked carboxy-hemoglobin solution;
reacting the o-ATP carboxy-hemoglobin with o-adenosine in an amount effective to effect predominantly intermolecular cross-linking of carboxy-hemoglobin, thus obtaining an intermolecularly and intramolecularly cross-linked carboxy-hemoglobin solution, and adding glutathione to the intermolecularly and intramolecularly cross-linked carboxy-hemoglobin solution to quench the o-adenosine cross-linking reaction; and
converting the cross-linked carboxy-hemoglobin in the intermolecularly and intramolecularly cross-linked carboxy-hemoglobin solution to cross-linked oxy-hemoglobin.

20. The method of claim 19, wherein the leukocyte-erythrocyte mixture is separated from the platelets and the plasma by centrifuging whole blood.

21. The method of claim 19, wherein the leukocyte aggregate is removed by filtration.

22. The method of claim 19, wherein the phospholipids and the precipitated non-heme proteins are removed from the carboxy-hemoglobin solution by solvent extraction.

23. The method of claim 19, wherein the concentrated carboxy-hemoglobin solution is concentrated by dialysis against an about normotonic solution.

24. A blood substitute, comprising the composition of claim 12; and
a pharmaceutically-acceptable saline solution.

25. The blood substitute of claim 24, wherein the cross-linked hemoglobin is dissolved in the pharmaceutically acceptable saline solution.

26. The composition of claim 12, in the form of a solution, wherein the solution further comprises mannitol.

27. A blood substitute comprising the composition of claim 12, being electrolyte-free.

28. The blood substitute of claim 27, wherein the cross-linked hemoglobin has a molecular weight of about 130,000 to 390,000.

29. The blood substitute of claim 27, wherein less than about 5% of the substantially pyrogen-free, microbe-free, active hemoglobin comprises met-hemoglobin.

30. The blood substitute of claim 27, wherein the cross-linked hemoglobin is further reacted with reduced glutathione.

31. The blood substitute of claim 30, wherein the hemoglobin, o-ATP, o-adenosine, and reduced glutathione are reacted in molar ratios of about 1:3:10:20.

32. The blood substitute of claim 27, wherein the substantially pyrogen-free, microbe-free, active hemoglobin comprises bovine hemoglobin.

33. The blood substitute of claim 27, prepared by a method comprising
converting hemoglobin in solution to carboxy-hemoglobin, thus obtaining a carboxy-hemoglobin solution;
pasteurizing the carboxy-hemoglobin solution to denature and precipitate non-heme proteins;
removing phospholipids and precipitated non-heme proteins from the carboxy-hemoglobin solution;
removing endotoxins from the carboxy-hemoglobin solution;
concentrating the carboxy-hemoglobin solution, thus obtaining a concentrated carboxy-hemoglobin solution;
predominantly intramolecularly cross-linking the carboxy-hemoglobin in the concentrated carboxy-hemoglobin solution with o-ATP, thus obtaining an intramolecularly cross-linked carboxy-hemoglobin solution;
predominantly intermolecularly cross-linking the o-ATP carboxy-hemoglobin in the intramolecularly cross-linked carboxy-hemoglobin solution with o-adenosine, thus obtaining an intermolecularly and intramolecularly cross-linked carboxy-hemoglobin solution;
adding reduced glutathione to the intermolecularly and intramolecularly cross-linked carboxy-hemoglobin solution to quench the o-adenosine cross-linking reaction;
converting the intermolecularly and intramolecularly crosslinked carboxy-hemoglobin in the intermolecularly and intramolecularly cross-linked carboxy-hemoglobin solution to cross-linked oxy-hemoglobin thus obtaining an electrolyte-free cross-linked oxy-hemoglobin solution.

34. The blood substitute of claim 33, wherein the hemoglobin solution is obtained by
separating whole blood into a leukocyte-erythrocyte mixture, platelets and plasma;
suspending the thus obtained leukocyte-erythrocyte mixture in an aqueous solution;
cooling the leukocyte-erythrocyte solution to aggregate the leukocytes and removing the leukocyte aggregate, thus obtaining a substantially leukocyte-free erythrocyte suspension;
dialyzing the substantially leukocyte-free erythrocyte suspension against a hypotonic solution to extract hemoglobin from erythrocytes in the substantially leukocyte-free erythrocyte suspension and obtain an extracted hemoglobin solution; and
separating the erythrocytes from the extracted hemoglobin solution by ultrafiltration under increased hydrostatic pressure.

35. The blood substitute of claim 27, wherein the o-ATP comprises periodate-oxidized ATP;
the o-adenosine comprises periodate-oxidized adenosine; and
the hemoglobin is intramolecularly cross-linked with the periodate-oxidized ATP and intermolecularly cross-linked with the periodate-oxidized adenosine to form polyhemoglobin.

36. The blood substitute of claim 35, further comprising a non-electrolyte.

37. A blood substitute formulation, comprising the composition of claim 12; and
a pharmaceutically-acceptable aqueous solution; the formulation being electrolyte-free.

38. The blood substitute formulation of claim 37, wherein the cross-linked hemoglobin is dissolved in the aqueous solution.

39. The blood substitute formulation of claim 38, comprising about 7.5 to 15 g of the blood substitute per dl of solution.

40. A method for preparing a composition suitable for use as a blood substitute, comprising converting hemoglobin in solution to carboxy-hemoglobin;
concentrating the carboxy-hemoglobin solution to about 10 g/dl;
reacting the carboxy-hemoglobin in the concentrated solution with o-ATP to effect predominantly intramolecular cross-linking of hemoglobin, thus obtaining an intramolecularly cross-linked carboxy-hemoglobin solution;
reacting the o-ATP carboxy-hemoglobin with o-adenosine to effect predominantly intermolecular cross-linking of hemoglobin, thus obtaining an intermolecularly and intramolecularly cross-linked carboxy-hemoglobin solution;
adding reduced glutathione to the intermolecularly and intramolecularly cross-linked carboxy-hemoglobin solution to quench the o-adenosine cross-linking reaction;
converting the cross-linked carboxy-hemoglobin in the intermolecularly and intramolecularly cross-linked carboxy-hemoglobin solution to cross-linked oxy-hemoglobin; and
forming a pharmaceutically acceptable cross-linked oxy-hemoglobin solution.

41. The method of claim 40, wherein the o-adenosine and o-ATP are prepared by periodate oxidation of adenosine and ATP; and
the periodate is removed from the o-adenosine and the o-ATP prior to reacting the o-ATP and the adenosine with the hemoglobin.

42. The method of claim 40, further comprising adding magnesium after converting the cross-linked carboxy-hemoglobin to oxyhemoglobin.

43. The method of claim 40, further comprising adding mannitol after converting the cross-linked carboxy-hemoglobin to oxyhemoglobin.

44. The method of claim 40, wherein the hemoglobin in solution is obtained from whole blood by separating whole blood into a leukocyte-erythrocyte mixture, platelets and plasma and suspending the thus obtained mixture in an aqueous solution;

cooling the aqueous solution comprising the leukocyte-erythrocyte mixture to aggregate the leukocytes and removing the leukocyte aggregate to obtain a substantially leukocyte-free erythrocyte solution;

dialyzing the substantially leukocyte-free erythrocyte solution against a hypotonic solution to extract hemoglobin from erythrocytes in the substantially leukocyte-free erythrocyte solution and separating the erythrocytes from the substantially leukocyte-free erythrocyte solution by ultrafiltration under increased hydrostatic pressure, thus obtaining an extracted hemoglobin solution;

converting the extracted hemoglobin in the extracted hemoglobin solution to carboxy-hemoglobin, thus obtaining a carboxy-hemoglobin solution;

pasteurizing the carboxy-hemoglobin solution to denature and precipitate non-heme proteins;

removing phospholipids and precipitated non-heme proteins from the carboxy-hemoglobin solution; and removing endotoxins from the carboxy-hemoglobin solution by affinity chromatography.

45. The method of claim 40, wherein the hemoglobin in solution is obtained from whole blood and the whole blood from which the hemoglobin in solution is obtained comprises bovine blood.

46. A purified hemoglobin composition prepared by the method of claim 45.

47. The method of claim 40, wherein the hemoglobin is converted to carboxy-hemoglobin by flushing carbon monoxide into the solution.

48. A method of preparing an electrolyte-free composition suitable for use as a blood substitute, comprising converting hemoglobin in solution to carboxy-hemoglobin, thus obtaining a carboxy-hemoglobin solution;

concentrating the carboxy-hemoglobin solution, thus obtaining a concentrated carboxy-hemoglobin solution;

predominantly intramolecularly cross-linking the carboxy-hemoglobin in the concentrated carboxy-hemoglobin solution with o-ATP, thus obtaining an intramolecularly cross-linked carboxy-hemoglobin solution;

predominantly intermolecularly cross-linking the carboxy-hemoglobin in the intramolecularly cross-linked carboxy-hemoglobin solution with o-adenosine, thus obtaining an intermolecularly and intramolecularly cross-linked carboxy-hemoglobin solution;

adding reduced glutathione to the intermolecularly and intramolecularly cross-linked carboxy-hemoglobin solution to quench the o-adenosine cross-linking reaction;

converting the intermolecularly and intramolecularly crosslinked carboxy-hemoglobin in the intermolecularly and intramolecularly cross-linked carboxy-hemoglobin solution to cross-linked oxy-hemoglobin, thus forming an aqueous, pharmaceutically-acceptable, electrolyte-free, cross-linked oxy-hemoglobin solution.

49. The method of claim 48, further comprising adding non-electrolytes and/or mannitol after converting the intermolecularly and intramolecularly cross-linked carboxy-hemoglobin to oxy-hemoglobin.

50. The method of claim 48, wherein the purified hemoglobin is obtained from whole blood by separating whole blood into a leukocyte-erythrocyte mixture, platelets and plasma;

suspending the thus obtained leukocyte-erythrocyte mixture in an aqueous solution;

cooling the leukocyte-erythrocyte solution to aggregate the leukocytes;

removing the leukocyte aggregate, thus obtaining a substantially leukocyte-free erythrocyte suspension;

dialyzing the substantially leukocyte-free erythrocyte suspension against a hypotonic solution to extract hemoglobin from erythrocytes in the substantially leukocyte-free erythrocyte suspension to obtain an extracted hemoglobin solution;

separating out the erythrocytes from the extracted hemoglobin solution by ultrafiltration under increased hydrostatic pressure;

converting the extracted hemoglobin in the extracted hemoglobin solution to carboxy-hemoglobin, thus obtaining a carboxy-hemoglobin solution;

pasteurizing the carboxy-hemoglobin solution to denature and precipitate non-heme proteins;

removing phospholipids and precipitated non-heme proteins from the carboxy-hemoglobin solution; and removing endotoxins from the carboxy-hemoglobin solution by affinity chromatography.

51. The method of claim 48, wherein the hemoglobin in solution is obtained from whole blood and the whole blood from which the hemoglobin in solution is obtained comprises bovine blood.

52. An electrolyte-free composition suitable for use as a blood substitute prepared by the method of claim 51.

* * * * *

UNITED STATES PATENT AND TRADEMARK OFFICE
CERTIFICATE OF CORRECTION

PATENT NO. : 5,439,882  
DATED : August 8, 1995  
INVENTOR(S) : M. Feola, et al

Page 1 of 3

It is certified that error appears in the above-indentified patent and that said Letters Patent is hereby corrected as shown below:

Page 1, Right Column 2, line 14 of the ABSTRACT:
  change "administrating" to --administering--.

Page 2, Left Column 1, line 25, under OTHER PUBLICATIONS:
  change "Aemrican" to --American--;
  Right Column 2, line 21;
  change "Feinstrone" to --Feinstone--;
  Right Column 2, line 25;
  change "Sanque" to --Sangue--.

In the Drawings:
Sheet 8 of the Drawings, Figure 8
  change "ADENSODINE" to --ADENOSINE--.

Column 2:
  line 36, change "tile" to --the--.

Column 3:
  line 36, change "rattler" to --rather--;
  line 51, change "tile" to --the--.

Column 4:
  line 53, change "tetramet" to --tetramer--.

UNITED STATES PATENT AND TRADEMARK OFFICE
CERTIFICATE OF CORRECTION

PATENT NO. : 5,439,882
DATED : August 8, 1995
INVENTOR(S) : M. Feola, et al

It is certified that error appears in the above-indentified patent and that said Letters Patent is hereby corrected as shown below:

Column 5:
    line 39, change "Feinston" to --Feinstone--.

Column 8:
    line 57, before "Abbott" insert --(--.

Column 9:
    line 10, change "Trasrusione" to --Trasfusione--.

Column 10:
    line 61, change "hands" to --bands--;
    line 68, change "Feinston" to --Feinstone--.

Column 16:
    line 32, change "p" to --μ--.

Column 17:
    line 45, change "tile" to --the--.

Column 21:
    line 22, change "tile" to --the--.

Column 23:
    line 13, delete the second occurrence of "only";
    line 62, change "tile" to --the--.

UNITED STATES PATENT AND TRADEMARK OFFICE
CERTIFICATE OF CORRECTION

PATENT NO. : 5,439,882
DATED : August 8, 1995
INVENTOR(S) : M. Feola, et al

It is certified that error appears in the above-indentified patent and that said Letters Patent is hereby corrected as shown below:

Column 25:
line 15, change "tile" to --the--;
line 66, change "mamomoles" to --nanomoes--.

Column 26:
line 1, change "fro" to --from--;
line 2, change "fro" to --from--.

Column 27:
line 1, change "tile" to --the--.

Column 28:
line 2, change "Tile" to --The--;
line 9, change "signs temperature pulse" to --signs, temperature, pulse,--;
line 49, change "GSB" to --GSH--;
line 57, change "with" to --without--.

Signed and Sealed this

Ninth Day of January, 1996

BRUCE LEHMAN

Attest:

Attesting Officer

Commissioner of Patents and Trademarks